United States Patent [19]

Cragoe, Jr. et al.

[11] 4,070,539

[45] Jan. 24, 1978

[54] [1-OXO-2-HALO(OR HYDROGEN) INDANYLOXY]-ALKANOIC ACID

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 683,362

[22] Filed: May 5, 1976

Related U.S. Application Data

[63] Continuation-in-part of Ser. No. 198,435, Nov. 2, 1971, abandoned, which is a continuation-in-part of Ser. No. 32,434, April 27, 1970, abandoned, which is a continuation-in-part of Ser. No. 778,840, Nov. 25, 1968, Pat. No. 3,704,314.

[51] Int. Cl.$^2$ .................................................. C07C 69/76
[52] U.S. Cl. .................................. 560/56; 260/308 D; 260/501.1; 260/501.16; 260/501.21; 260/516; 260/546; 260/558 S; 260/559 B; 560/10; 424/308
[58] Field of Search ...................... 260/520 C, 473 F

[56] References Cited

U.S. PATENT DOCUMENTS

| | | | |
|---|---|---|---|
| 3,668,241 | 6/1972 | Crayoe et al. | 260/520 C |
| 3,984,465 | 10/1976 | Crayoe et al. | 260/520 C |

*Primary Examiner*—Paul J. Killos
*Attorney, Agent, or Firm*—Michael C. Sudol, Jr.

[57] ABSTRACT

[1-Oxo-2-halo(or hydrogen)indanyloxy(or thio)]-alkanoic acid products and salts, esters and amide derivatives where the indanyl ring may be further substituted with from 2 to 5 nuclear substituents. The [1-oxo-2-haloindanyloxy-(or thio)]alkanoic acids are prepared (1) via the halogenation of a [1-oxoindanyloxy(or thio)]alkanoic acid or (2) via the addition of halogen to a [1-oxoindenyloxy(or thio)]-alkanoic acid. The [1-oxoindanyloxy(or thio)]alkanoic acids are prepared (1) via cyclialkylation of a (2-alkylideneacyl)-phenoxy(or thio)alkanoic acid or (2) via etherification of a hydroxy(or mercapto)-2-alkyl-1-indanone. The [1-oxo-2-halo(or hydrogen)indanyloxy(or thio)]alkanoic acids are diuretics and saluretics. In addition, some of these compounds are also able to maintain the uric acid concentration in the body at pretreatment level or to cause a decrease in uric acid concentration.

13 Claims, No Drawings

[1-OXO-2-HALO(OR HYDROGEN) INDANYLOXY]-ALKANOIC ACID

This is a continuation-in-part of U.S. application Ser. No. 198,435 filed Nov. 2, 1971, abandoned which is a continuation-in-part of U.S. application Ser. No. 32,434 filed Apr. 27, 1970, now abandoned, which is a continuation-in-part of U.S. application Ser. No. 778,840 filed Nov. 25, 1968, now U.S. Pat. No. 3,704,314.

This invention relates to a new class of chemical compounds which can be described generally as [1-oxo-2-halo(or hydrogen)indanyloxy]alkanoic acids and [1-oxo-2-halo(or hydrogen)indanylthio]alkanoic acids and to the nontoxic, pharmacologically acceptable salts, esters and amide derivatives thereof. It is also an object of this invention to describe novel methods for the preparation of the [1-oxo-2-halo(or hydrogen)indanyloxy]-alkanoic acids and [1-oxo-2-halo-(or hydrogen)indanylthio]alkanoic acids. Pharmacological studies show that the instant products are effective diuretic and saluretic agents which can be used in the treatment of conditions associated with electrolyte and fluid retention and hypertension. More importantly, some of these compounds are able to maintain the uric acid concentration at pretreatment level or to even cause a decrease in the uric acid concentration.

When administered in therapeutic dosages, in conventional vehicles, the instant products effectively reduce the amount of sodium and chloride ions in the body, lower dangerous excesses of fluid levels to acceptable levels and, in general, alleviate conditions usually associated with edema. In addition, those compounds containing a 2-alkyl or 2-cycloalkyl substituent and which may also contain a 2-chloro or 2-fluoro substituent overcome a major problem associated with many of the presently available diuretics and saluretics. Many of the presently available diuretics and saluretics have a tendency upon administration to precipitate uric acid in the body and thereby cause from mild to severe cases of gout. Many of the instant compounds described below now provide a tool to treat those patients requiring diuretic and saluretic treatment without the risk of inducing gout.

The [1-oxo-2-halo(or hydrogen)indanyloxy]alkanoic acids and [1-oxo-2-halo(or hydrogen)indanylthio]alkanoic acids of the invention are compounds having the following structural formula:

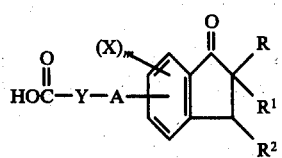

I wherein A is oxygen or sulfur; R is lower alkyl containing from 1 to 5 carbon atoms such as methyl, ethyl, n-propyl, isopropyl, n-butyl, sec-butyl, isobutyl, pentyl and the like, cycloalkyl, for example, cycloalkyl containing from 3 to 6 nuclear carbon atoms such as cyclopropyl, cyclobutyl, cyclopentyl, cyclohexyl and the like or mononuclear aralkyl, for example, phenyl lower alkyl such as benzyl and the like or halo substituted mononuclear aralkyl, for example, halo substituted phenyl lower alkyl such as 4-chlorobenzyl and the like or trifluoro substituted lower alkyl such as 2,2,2-trifluoroethyl and the like; $R^1$ is hydrogen or halo such as chloro, bromo, fluoro and the like; $R^2$ is hydrogen, halogen, for example, chloro, bromo, iodo and the like, lower alkyl, for example, methyl, ethyl and the like or phenyl; Y is an alkylene or haloalkylene radical having a maximum of 4 carbon atoms and which contain from 1 to 3 linear carbon atoms between the carboxy and oxy or thio moieties embraced by the definition of A, as, for example, methylene ethylidene, propylidene, isopropylidene, ethylene, trimethylene, fluoromethylene and the like; the X radicals are similar or dissimilar members selected from halogen such as fluoro, bromo, chloro, iodo and the like; lower alkyl such as methyl, ethyl, n-propyl, isopropyl, n-butyl and the like; trihalomethyl such as trifluoromethyl and the like; acylamino, for example, lower alkanoylamino such as acetylamino and the like and, taken together, two X radicals on adjacent carbon atoms of the benzene ring may be joined to form a hydrocarbylene chain (i.e., a divalent organic radical composed solely of carbon and hydrogen) containing from 3 to 4 carbon atoms between their points of attachment, for example, trimethylene, tetramethylene, 1,3-butadienylene (i.e., —CH=CH—CH—CH—) and the like, and m is an integer having a value of 1 to 3 with the proviso that when X is lower alkyl m is an integer of 2 and 3. Also included are the lower alkyl ester and amide derivatives therefore.

A preferred embodiment of this invention relates to [1-oxo-2-halo(or hydrogen)-5-indanyloxy]acetic acids having the following structural formula:

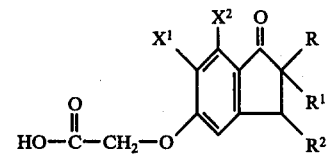

wherein R is lower alkyl containing from 1 to 5 carbon atoms such as methyl, ethyl, n-propyl, isopropyl, n-butyl, secbutyl, isobutyl, pentyl, and the like; or trifluoro substituted lower alkyl such as 2,2,2-trifluoroethyl and the like; cycloalkyl having from 3 to 6 nuclear carbon atoms, cycloalkyl lower alkyl containing from 3 to 6 nuclear carbon atoms in the cycloalkyl moiety such as cyclopropyl, cyclobutyl, cyclopentyl, cyclohexyl and the like; phenyl lower alkyl such as benzyl and the like or halo substituted phenyl lower alkyl such as 4-chlorobenzyl and the like; $R^1$ is hydrogen or halo such as chloro, bromo, fluoro and the like; $R^2$ is hydrogen, halogen, for example, chloro, bromo, iodo and the like, or lower alkyl, for example, methyl, ethyl and the like; $X^1$ is hydrogen; halogen such as fluoro, bromo, chloro, iodo and the like; lower alkyl such as methyl, ethyl, n-propyl, isopropyl, n-butyl and the like; trihalomethyl such as trifluoromethyl and the like; $X^2$ is halogen such as fluoro, bromo, chloro, iodo and the like; lower alkyl such as methyl, ethyl, n-propyl, isopropyl, n-butyl and the like; trihalomethyl such as trifluoromethyl and the like or $X^1$ and $X^2$ may be joined to form a 1,3-butadienyl linkage (i.e., —CH=CH—CH=CH—) and the nontoxic, pharmacologically acceptable salt, lower alkyl ester and amide, derivatives thereof. The foregoing class of compounds exhibit particularly good diuretic and saluretic activity and represents a preferred subgroup within the scope of this invention.

Another preferred embodiment of this invention relates to [1-oxo-2-halo(or hydrogen)-5-indanyloxy]acetic acids having the following structural formula:

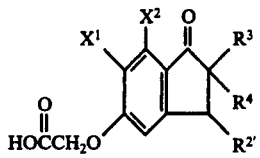

wherein R[2'] is hydrogen of phenyl; R[3] is lower alkyl containing 2 to 4 carbon atoms such as ethyl, n-propyl, isopropyl, tert-butyl and the like or cycloalkyl containing 3 to 6 carbon atoms such as cyclopropyl, cyclobutyl, cyclopentyl or cyclohexyl; R[4] is hydrogen, chloro or fluoro and X[1] and X[2] represent similar or dissimilar members selected from hydrogen, halogen, methyl or, taken together, X[1] and X[2] may be joined to form a 1,3-butadienylene linkage (i.e., —CH=CH—CH=CH—) with proviso that X[1] and X[2] cannot both by hydrogen at the same time and when one of the X[1] or X[2] radicals is methyl the other X[1] and X[2] radical is other than hydrogen and to the nontoxic, pharmacologically acceptable salts, esters and amide derivatives thereof.

A further preferred embodiment of this invention relates to [1-oxo-2-halo(or hydrogen)-5-indanyloxy]acetic acids having the structure (Ia) wherein R[2'] is hydrogen; R[3] is lower alkyl containing from 2 to 4 carbon atoms such as ethyl, n-propyl, isopropyl and the like or cycloalkyl containing from 3 to 6 carbon atoms such as cyclopropyl, cyclobutyl, cyclopentyl, or cyclohexyl; R[4] is hydrogen, chloro or fluoro and X[1] and X[2] represent similar or dissimilar members selected from methyl or halogen such as fluoro and chloro and the nontoxic, pharmacologically acceptable salt and lower alkyl ester and amide derivatives thereof. The foregoing class of compounds exhibits particularly good diuretic and saluretic activity and represents a further preferred subgroup of compounds within the scope of this invention.

A still further preferred embodiment of this invention relates to [1-oxo-2-halo(or hydrogen)-5-indanyloxy]acetic acids having the structure (Ia) wherein R[3] is cycloalkyl containing 3 to 6 carbon atoms such as cyclopropyl, cyclobutyl, cyclopentyl or cyclohexyl or lower alkyl containing 2 to 4 carbon atoms of the formula CHR[7]R[8] wherein R[7] is hydrogen or a lower alkyl having from 1 to 2 carbon atoms such as methyl or ethyl and R[8] is a lower alkyl having from 1 to 3 carbon atoms such as methyl, ethyl, n-propyl or isopropyl with the proviso that the total number of carbon atoms in R[7] and R[8] does not exceed three; R[4] is hydrogen, chloro or fluoro; R[2'] is hydrogen; X[1] and X[2] represent similar or dissimilar members selected from methyl or halogen such as fluoro and chloro and the nontoxic, pharmacologically acceptable salts, lower alkyl ester and amide derivatives thereof. The foregoing class of compounds exhibits particularly good diuretic and saluretic activity and represents a further preferred subgroup of compounds within the scope of this invention. A further preferred embodiment are those compounds just described where X[1] and X[2] are halo.

A still further preferred embodiment of this invention relates to [1-oxo-2-halo(or hydrogen)-5-indanyloxy]acetic acid having the structure (Ia) wherein R[3] is lower alkyl containing 2 to 4 carbon atoms such as ethyl, n-propyl, isopropyl, n-butyl and the like or cycloalkyl containing 5 to 6 carbon atoms such as cyclopentyl and cyclohexyl; R[4] is hydrogen or chloro; R[2'] is hydrogen and X[1] and X[2] are halo such as fluoro or chloro but preferably chloro, and the nontoxic, pharmacologically acceptable salts, esters and amide derivatives thereof.

The foregoing class of compounds exhibits particularly good diuretic and saluretic activity and represents a preferred subgroup of compounds within the scope of this invention.

The [1-oxo-2-haloindanyloxy(or thio)]alkanoic acids (II, infra) may be prepared by the halogenation of an appropriate ]1-oxoindanyloxy(or thio)]alkanoic acid (III, infra) with a halogenating agent such as bromine, chlorine, sulfuryl chloride or cupric chloride. In this regard, when bromine is the halogenating agent employed, it has been found most beneficial to add a trace of 48% hydrobromic acid to initiate the reaction. In general, any solvent which is substantially inert with respect to the reactants employed and in which the reagents are reasonably soluble may be used. Solvents which have proved to be particularly advantageous include acetic acid, chloroform, dioxane, diethyl ether, methylene chloride and the like. The reaction may be conducted at temperatures of from about 0° to about 100° C. The following equation illustrates this process:

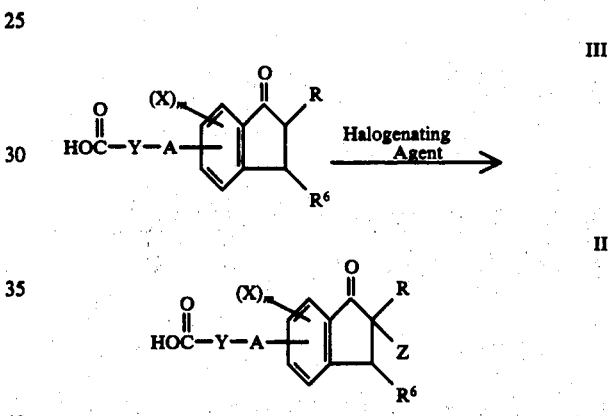

wherein A, R, m, X and Y are as defined above and R[6] is hydrogen, lower alkyl or phenyl and Z is halogen.

Still another method for the preparation of the [1-oxo-2-haloindanyloxy(or thio)]alkanoic acid products (II) consists of the addition of halogen to a corresponding (1-oxoindenyloxy)alkanoic acid with a halogenating agent. With this method a halogen is also introduced in the 3-position. Suitable halogenating agents include chlorine, bromine and the like in an alkanoic acid such as acetic acid and the like. The following equation illustrates this process; however, it is to be understood that the chlorine reagent depicted is simply illustrative of the type of reagent that may be employed and in practice any other functionally equivalent reagent could be substituted therefor in an otherwise similar reaction to afford the corresponding nuclear halogenated product:

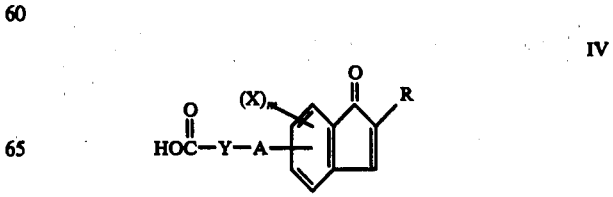

-continued

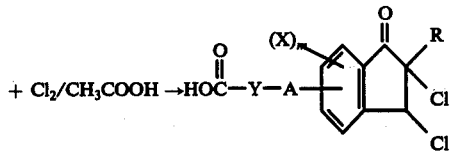

wherein A, Y, R, X and m are as defined above. The (1-oxoindenyloxy)alkanoic acids (IV) employed as starting materials in this synthesis are the subject of applicants' U.S. Pat. No. 3,668,241.

The [1-oxoindanyloxy(or thio)]alkanoic acids (III, infra) are themselves diuretically active and as described above in the preferred embodiment also exhibit the ability to either maintain uric acid concentration at pretreatment level or to cause a decrease in uric acid concentration and are prepared by cyclialkylation of the appropriate [(2-alkylindeneacyl)phenoxy(or phenylthio)]alkanoic acid (V, infra) using an electron-acceptor acid, for example, a Lewis acid such as concentrated sulfuric acid, polyphosphoric acid, boron trifluoride and the like. The reaction may be conducted at ambient temperatures but, generally, it is desirable to conduct the reaction at temperatures above ambient temperature. The following equation illustrates this process:

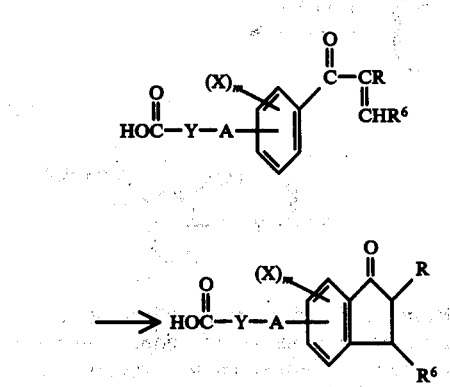

wherein A, R, $R^6$, m, X and Y are as defined above.

The [1-oxo-2-alkylindanyloxy(or thio)]alkanoic acids (III) may also be prepared by etherification. The etherification method comprises reacting a haloalkanoic acid or ester of the formula:

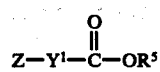

wherein Z is as defined above, $Y^1$ is methylene or trimethylene which may be substituted by alkyl or fluoro and $R^5$ is hydrogen or lower alky such as methyl, ethyl and the like with a suitable hydroxy(or mercapto)-2-alkyl-1-indanone (VI, infra). The following equation illustrates this reaction:

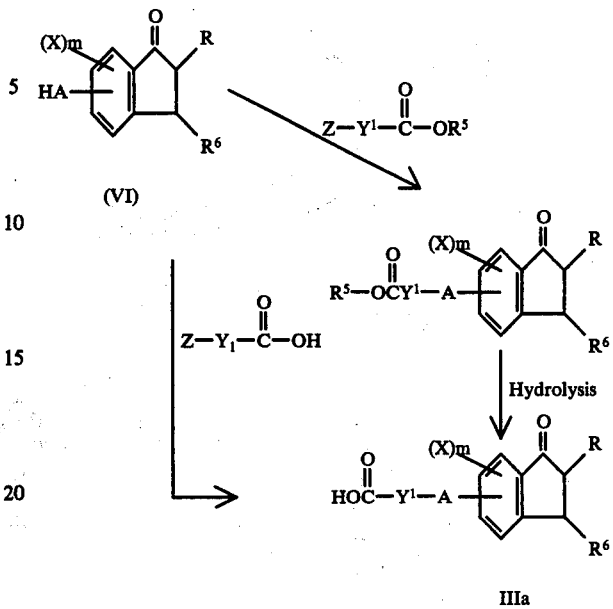

wherein A, R, $R^6$, $R^5$, $Y^1$, m and Z are as defined above. Also, it will be noted that inasmuch as the definition of the $Y^1$ is limited solely to methylene or trimethylene, which may be substituted by alkyl or fluoro, the [1-oxo-2-alkylindanyloxy(or thio)]alkanoic acid or esters produced by this process contain only a single carbon atoms or, alternatively, three linear carbon atoms between the carbonyl and oxygen (or thio) group. In general, the reaction is conducted in the presence of a base as potassium or sodium carbonate or potassium or sodium hydroxide or in the presence of a sodium alkoxide such as sodium ethoxide. The choice of a suitable reaction solvent is largely dependent upon the character of the reactants employed but, in general, any solvent which is substantially inert to the reactants and in which the reagents are reasonably soluble may be used; ethanol and dimethylformamide, for example, have proved to be particularly advantageous solvents in which to conduct the reaction. The process may be carried out at ambient temperature but, generally, it is desirable to conduct the process at a temperature above ambient temperature. If the ester is obtained it may be hydrolyzed to the free acid by methods well known to those skilled in the art.

The [2-(alkylideneacyl)phenoxy(or phenylthio)]-alkanoic acid intermediates of the instant process (V, supra) are either known compounds or may be prepared by methods known to those skilled in the art. Thus, for example, the [(2-methyleneacyl)phenoxy or phenylthio)]-alkanoic acid intermediates (Va, infra) are prepared by the reaction of an appropriate alkanoylphenoxy(or phenylthio)alkanoic acid (VII, infra) with dimethylamine hydrochloride and paraformaldehyde to afford the corresponding Mannich amine salt (VIII, infra) which, upon treatment with sodium bicarbonate, yields the desired [(2-methyleneacyl)-phenoxy(or phenylthio)]alkanoic acid (Va, infra). The following equation illustrates this method:

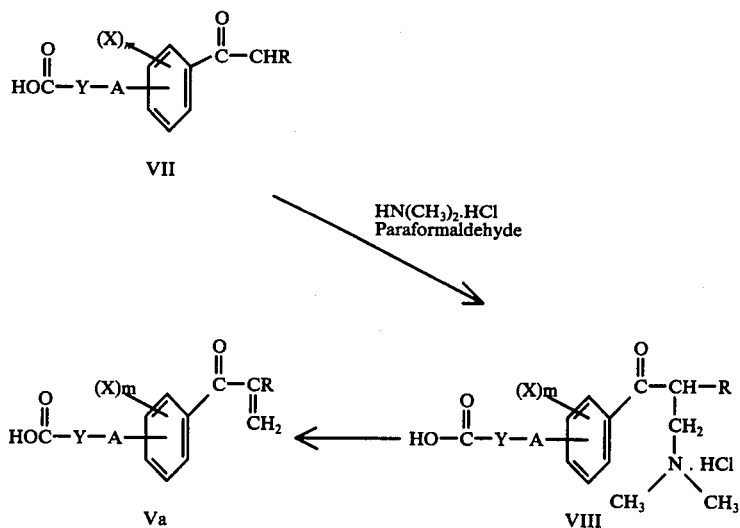

wherein A, R, m, X and Y are as defined above.

The hydroxy(or mercapto)-1-indanones (VI) are prepared by the cyclialkylation of an appropriately substituted 2-(alkylideneacyl)phenol(or thiophenol) (IX, infra) by treatment with an electron-acceptor acid, for example, a Lewis acid such as concentrated sulfuric acid, polyphosphoric acid, boron trifluoride and the like. The reaction may be conducted at ambient temperatures but, generally, it is desirable to conduct the reaction at temperatures above ambient temperatures. The following equation illustrates this process:

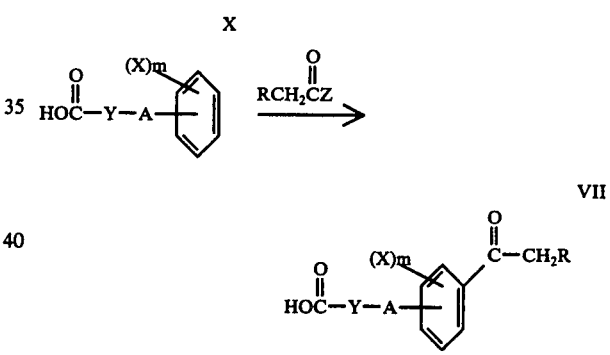

wherein A, R, R⁶, m and X are as defined above.

The nuclear substituted alkanoylphenoxy(or phenylthio)alkanoic acids (VII, infra) are either known compounds or may be prepared by a variety of methods but, generally, the most advantageous route consists in the reaction of an alkanoyl halide with the appropriate phenoxy(or phenylthio)alkanoic acid (X, infra) in the presence of a Friedel-Crafts catalyst such as aluminum chloride to produce the corresponding alkanoylphenoxy(or phenylthio)alkanoic acids. The reaction solvent and the temperature at which the reaction is conducted are not particularly critical aspects of the reaction inasmuch as any solvent which is inert to the acid halide and phenoxy(or phenylthio)alkanoic acid reactants and Friedel-Crafts catalyst may be employed with good results and the reaction temperature may be varied to obtain the desired rate of reaction. In this regard, it has been found that carbon disulfide and methylene chloride are particularly suitable solvents in which to conduct the reaction and that the reaction proceeds most advantageously with slight heating as, for example, by heating at the reflux temperature of the solvent employed. The following equation illustrates this reaction:

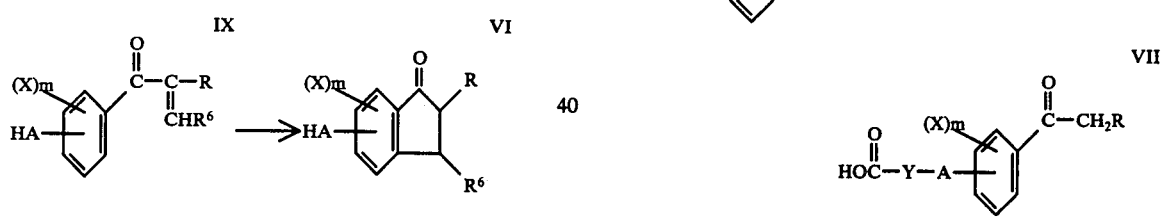

wherein A, R, m, X, Y and Z are as defined above.

The 2-(alkylideneacyl)phenol(and thiophenol) intermediates (IX, supra) are either known compounds or may be prepared by the Mannich reaction in the manner similar to that described for the preparation of [2-(methyleneacyl)-phenoxy(or phenylthio)]alkanoic acid (Va, supra), i.e., by the reaction of an alkanoylphenol(or thiophenol) (XI, infra) with dimethylamine hydrochloride and paraformaldehyde followed by treatment of the intermediate (XIa, infra) thus obtained with aqueous sodium bicarbonate or anhydrous dimethylformamide either with or without heat to afford the desired phenol or thiophenol (IX). The following equation illustrates this process:

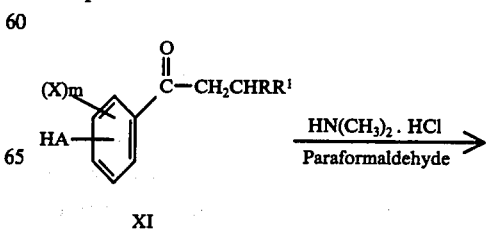

-continued

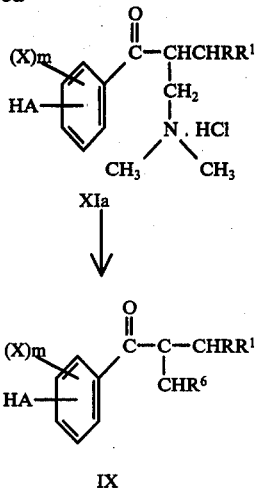

wherein A, R, R¹, m and X are as defined above and R⁶ is hydrogen.

Included within the scope of this invention are the nontoxic, pharmacologically acceptable salts of the instant products. In general, any base which will form a salt with the foregoing [1-oxo-2-halo(or hydrogen)indanyloxy(or thio)]alkanoic acids and whose pharmacological properties will not cause an adverse physiological effect when ingested by the body system is considered as being within the scope of this invention; suitable bases thus include, for example, the alkali metal and alkaline earth metal hydroxides, carbonates and bicarbonates, ammonia, primary, secondary and tertiary amines, such as mono-lower alkyl amines, di-lower alkyl amines, tri-lower alkyl amines, quaternary ammonium hydroxides, nitrogen-containing heterocyclic amines containing from 4 to 6 carbon atoms and the like. Especially preferred metal cations are those derived from alkali metals, e.g., sodium, potassium, lithium, and the like and alkaline earth metals, e.g., calcium, magnesium, and the like and other metals, e.g., aluminum, iron and zinc. These salts are prepared by conventional methods well known in the art. Thus, the acid upon reaction with alkali metal and alkaline earth metal hydroxides, carbonates, bicarbonates, amines or quarternary ammonium hydroxyides, forms the corresponding alkali metal, alkaline earth metal, amine or quarternary ammonium salt.

Pharmaceutically acceptable salts can be formed from ammonia, primary, secondary, or tertiary amines, or quaternary ammonium hydroxides such as methylamine, dimethlamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tri(hydroxymethyl)aminomethane, N-methylglucamine, N-methylglucosamine, ephedrine, procaine, tetramethylammonium hydroxide, tetraethylammonium hydroxide, benzyltrimethylammonium and the like.

The salts recited above are particularly useful as parenteral solutions because they are very soluble in pharmaceutical carriers such as water or alcohol.

The anhydride derived from the carboxylic acids of the present invention are included in the invention.

Also included within the scope of this invention are the ester and amide derivatives of the instant products which are prepared by conventional methods well known to those skilled in the art. Thus, for example, the ester derivative may be prepared by the reaction of a [1-oxo-2-halo(or hydrogen)indanyloxy(or thio)]alkanoic acid of this invention with an alcohol as, for example, with a lower alkanol. The amide derivatives may be prepared by converting a [1-oxo-2-halo(or hydrogen)indanyloxy(or thio)]-alkanoic acid to its corresponding acid chloride by treatment with thionyl chloride followed by treating said acid chloride with ammonia, an appropriate mono-lower alkyl amine, di-lower alkyl amine or a hetero amine, such as piperidine, morpholine and the like to produce the corresponding amide compound. These and other equivalent methods for the preparation of the ester and amide derivatives of the instant products will be apparent to one having ordinary skill in the art and to the extent that said derivatives are both nontoxic and physiologically acceptable to the body system, said derivatives are the functional equivalent of the corresponding [1-oxo-2-halo(or hydrogen)indanyloxy(and thio)]alkanoic acids.

In addition to the salts, esters and amides being functionally equivalent to the carboxylic products those compounds wherein the carboxylic acid is replaced by a tetrazolyl radical are also functionally equivalent to the carboxylic acids. These tetrazole analogs are prepared as depicted in the following equation:

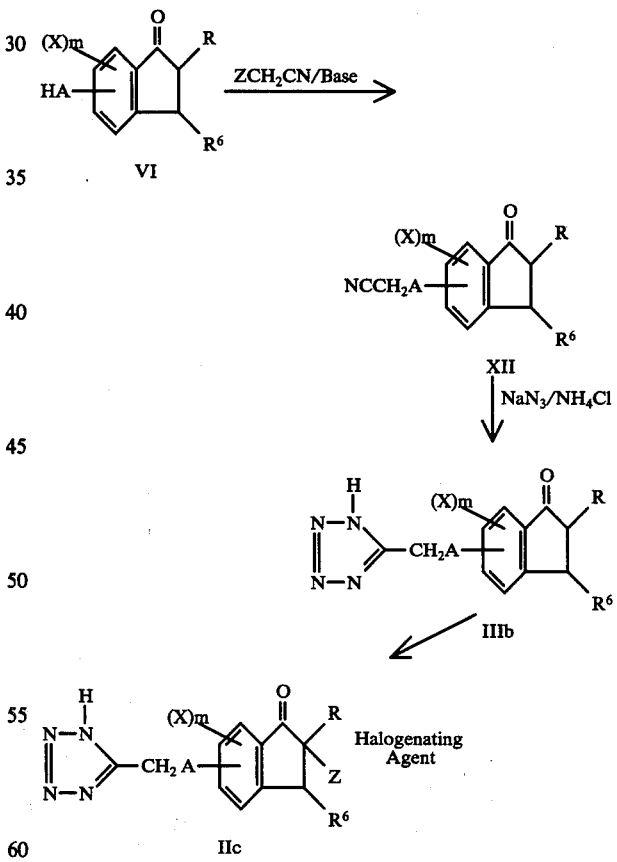

wherein A, R, R⁶, X, m and Z are as defined above.

The hydroxy(or mercapto)-1-indanone (VI) is treated with a haloacetonitrile such as chloroacetonitrile, bromoacetonitrile or iodoacetonitrile in the presence of a base such as potassium carbonate and the like in a suitable solvent such as acetone, dimethylformamide, dimethoxyethane and the like at a temperature in the range of from 25° to 100° C. to afford the corresponding nitrile (XII, supra) which upon treatment with sodium azide, ammonium chloride in dimethylformamide at a temperature in the range of from 25°–100° C. affords the 5-[1-oxoindanyloxy(or thio)methyl]tetrazole (IIIb, supra) which can be halogenated in the manner described above to afford the 5-[1-oxo-2-haloindanyloxy(or thio)-methyl]-tetrazole (IIc, supra).

The examples which follow illustrate the [1-oxo-2-halo(or hydrogen)indanyloxy(and thio)]alkanoic acid products (I) of the invention and the methods by which they are prepared. However, the examples are illustrative only and it will be apparent to those having ordinary skill in the art that all of the products embraced by formula I, supra, may also be prepared in an analogous manner by substituting the appropriate starting materials for those set forth in the examples.

EXAMPLE 1

(1-Oxo-2-bromo-2-ethyl-6,7-dichloro-5-indanyloxy)acetic Acid

Step A: (1-Oxo-2-ethyl-6,7-dichloro-5-indanyloxy)acetic Acid

[2,3-Dichloro-4-(2-methylenebutyryl)phenoxy]acetic acid (100 g.) is added with stirring to concentrated sulfuric acid (95–98%, 500 ml.) and the mixture is heated at 60° C. for six hours. The reaction mixture is then cooled and poured into a mixture of ice and water (4 l.) and the crude product which separates is ground in a mortar, filtered, washed with water and dried. After recrystallization from acetic acid (450 ml.) there is obtained 56 g. (56%) of (1-oxo-2-ethyl-6,7-dichloro-5-indanyloxy)acetic acid which melts at 171°–172° C.

Elemental analysis for $C_{13}H_{12}Cl_2O_4$: Calc.: C, 51.51; H, 3.99; Cl, 23.39; Found: C, 52.01; H, 3.90; Cl, 23.14.

Step B: (1-Oxo-2-bromo-2-ethyl-6,7-dichloro-5-indanyloxy)acetic Acid

To a stirred suspension of (1-oxo-2-ethyl-6,7-dichloro-5-indanyloxy)acetic acid (30.3 g., 0.10 moles) in acetic acid (300 ml.) is added a solution of bromine (16.0 g., 0.10 moles) in acetic acid (50 ml.) over a period of 30 minutes. The reaction is catalyzed by the addition of 48% aqueous hydrobromic acid (2 drops). The clear yellow solution is stirred at room temperature for 30 minutes then poured into ice water (1 l.) containing sodium bisulfite (2 g.). The crude (1-oxo-2-bromo-2-ethyl-6,7-dichloro-5-indanyloxy)acetic acid (36 g., 97%) thus obtained is filtered, washed with water and dried. It melts at 189°–191° C. after recrystallization from a mixture of ethyl acetate and hexane.

Elemental analysis for $C_{13}H_{11}BrCl_2O_4$: Calc: C, 40.87; H, 2.90; Br, 20.92; Cl, 18.56; Found: C, 41.21; H, 3.17; Br, 20.71; Cl, 18.38.

EXAMPLE 2

(1-Oxo-2-bromo-2-ethyl-6-chloro-5-indanyloxy)acetic Acid Step A: (2-Chloro-4-butyrylphenoxy)acetic Acid A one liter three-necked flask fitted with a stirrer, condenser and drying tube is charged with (o-chlorophenoxy)-acetic acid (37.2 g., 0.20 mole), carbon disulfide (400 ml.) and butyryl chloride (26.7 g., 0.25 mole). Aluminum chloride (86.9 g., 0.65 mole) is added to the reaction mixture during one hour. The reaction mixture is stirred one hour at 25° C., two hours at 55° C. and then cooled. The carbon disulfide is decanted and the product is poured onto a mixture of ice (300 g.) and concentrated hyrochloric acid (50 ml.). The product is extracted into ether, washed with water, dried over magnesium sulfate and distilled at reduced pressure to leave 36 g. (71%) of (2-chloro-4-butyrylphenoxy)acetic acid which melts at 113°–114° C. after recrystallization from butyl chloride.

Elemental analysis for $C_{12}H_{13}ClO_4$: Calc: C, 56.15; H, 5.10; Cl, 13.81; Found: C, 56.14; H, 5.13; Cl, 13.97.

Step B: [2-Chloro-4-(2-dimethylaminomethylbutyryl)-phenoxy]acetic Acid Hydrochloride (2-Chloro-4-butyrylphenoxy)acetic acid (12.8 g., 0.05 mole), paraformaldehyde (1.65 g., 0.055 mole), dimethylamine hydrochloride (4.62 g., 0.056 mole) and acetic acid (1ml.) are combined and heated on a steam bath for three hours. The reaction mixture is treated with ethyl alcohol (75 ml.) and ether (125 ml.) which causes precipitation of 11.7 g. (69%) of [2-chloro-4-(2-dimethylaminomethylbutyryl)phenoxy]acetic acid hydrochloride which melts at 182° C. after recrystallization from 2-propanol (90 ml.).

Elemental analysis for $C_{15}H_{21}Cl_2NO_4$: Calc: C, 51.44; H, 6.04; N, 4.00; Found: C, 51.52; H, 6.11; N, 3.97.

Step C: [2-Chloro-4-(2-methylenebutyryl)phenoxy]acetic Acid

[2-Chloro-4-(2-dimethylaminomethylbutyryl)-phenoxy]acetic acid hydrochloride (8.7 g., 0.025 mole), water (100 ml.), and saturated aqueous sodium bicarbonate (100 ml.) are combined and heated on a steam bath for 2.5 hours. The reaction mixture is acidified, extracted with ether and dried over magnesium sulfate. Distillation of the solvent at reduced pressure leaves 1.3 g. (20%) of [2-chloro-4-(2-methylenebutyryl)phenoxy]acetic acid which melts at 83.5°–85.5° C. after recrystallization from methyl cyclohexane (75 ml.).

Elemental analysis for $C_{13}H_{13}ClO_4$: Calc.: C, 58.11; H, 4.88; Cl, 13.20; Found: C, 57.80; H, 5.20; Cl, 13.00.

Step D: Preparation of (1-Oxo-2-ethyl-6-chloro-5-indanyloxy)acetic Acid (1-Oxo-2-ethyl-6-chloro-5-indanyloxy)acetic acid is prepared by following substantially the same procedure as described in Example 1, Step A, using the following reagents: [2-chloro-4-(2-methylenebutyryl)phenoxy]acetic acid (41.32 g., 0.154 mole) and conc. sulfuric acid (165 ml.). The crude yield of the product is 38.8 g. (94%), m.p. 132°–138° C. Recrystallization from benzene gives (1-oxo-2-ethyl-6-chloro-5-indanyloxy)acetic as white prisms, m.p. 142°–144° C.

Elemental analysis for $C_{13}H_{13}ClO_4$: Calc.: C, 58.11; H, 4.88; Cl, 13.20; Found: C, 58.14; H, 4.76; Cl, 13.45.

Step E: (1-Oxo-2-bromo-2-ethyl-6-chloro-5-indanyloxy)-acetic Acid (1-Oxo-2-bromo-2-ethyl-6-chloro-5-indanyloxy)acetic acid is prepared by following substantially the same procedure as described in Example 1, Step B, using the following reagents: (1-oxo-2-ethyl-6-chloro-5-indanyloxy)acetic acid (13.44 g., 0.05 mole), bromine (8.79 g., 0.055 mole), acetic acid (135 ml.) and 48% hydrobromic acid (2 drops). The crude yield of the product is 17.38 g. (100%), m.p. 157°–159° C. Recrystallization from benzene gives (1-oxo-2-bromo-2-ethyl-6-chloro-5-indanyloxy)acetic acid as white needles, m.p. 159.5°–160.5° C.

Elemental analysis for $C_{13}H_{12}BrClO_4$: Calc.: C, 44.92; H, 3.48; Cl, 10.20; Found: C, 45.04; H, 3.45; Cl, 10.21.

EXAMPLE 3

(1-Oxo-2-bromo-2-ethyl-4,6,7-trimethyl-5-indanyloxy)acetic Acid

Step A: (1-Oxo-2-ethyl-4,6,7-trimethyl-5-indanyloxy)-acetic Acid

Finely ground [2,3,6-trimethyl-4-(2-methylenebutyryl)-phenoxy]acetic acid (12.18 g., 0.044 mole) is added portionwise, over a period of one hour, to concentrated sulfuric acid (49 ml.) at room temperature. The resulting reddishbrown solution is allowed to stand in the refrigerator at 0° C. for six days.

The reaction solution is added dropwise to ice water (245 ml.) and the crude product (11.6 g., 96%) is collected, dried and recrystallized from butyl chloride to yield substantially pure (1-oxo-2-ethyl-4,6,7-trimethyl-5-indanyloxy)-acetic acid, m.p. 136°–137° C.

Elemental analysis for $C_{16}H_{20}O_4$: Calc.: C, 69.54; H, 7.30; Found: C, 69.74; H, 7.14.

Step B: (1-Oxo-2-bromo-2-ethyl-4,6,7-trimethyl-5-indanyloxy)acetic Acid (1-Oxo-2-bromo-2-ethyl-4,6,7-trimethyl-5-indanyloxy)-acetic acid is prepared by following substantially the same procedure as described in Example 1, Step B, using the following reagents: (1-oxo-2-ethyl-4,6,7-trimethyl-5-indanyloxy)-acetic acid (11.79 g., 0.0427 mole), bromine (7.51 g., 0.0470 mole), acetic acid (118 ml.) and 48% hydrobromic acid (2 drops). The crude yield is 14.76 g. (97%). Recrystallization from butyl chloride give (1-oxo-2-bromo-2-ethyl-4,6,7-trimethyl-5-indanyloxy)acetic acid as white prisms, m.p. 144°–145° C.

EXAMPLE 4

(1Oxo-2-bromo-2-ethyl4-chloro-7indanyloxy)acetic Acid

Step A: (1-Oxo-2-ethyl-4-chloro-7indanyloxy)acetic Acid [2-(2-Methylenebutyryl)-4-chlorophenoxy]acetic acid (35.5 g., 0.132 mole) and conc. sulfuric acid (125 ml.) are mixed and allowed to stand at room temperature. After 5 days, the reaction mixture is poured into cold water (1500 ml.). The solid that separates is collected, washed well with water, dried and recrystallized from acetic acid to yield 23 g. (65%) of (1-oxo-2-ethyl-4-chloro-7-indanyl-oxy)acetic acid, m.p. 154°–163° C. This is the material used for subsequent bromination. A small sample of (1-oxo-2-ethyl-4-chloro-7-indanyloxy)acetic acid is further recrystallized from acetic acid, m.p. 161°–167° C.

Elemental analysis for $C_{13}H_{13}ClO_4$: Calc.: C, 58.11; H, 4.87; Found: C, 58.39; H, 4.77.

Step B: (1-Oxo-2-bromo-2-ethyl-4-chloro-7indanyloxy)-acetic Acid

Bromine (13 g., 0.081 mole) is added dropwise for 20 minutes to a solution of (1-oxo-2-ethyl-4-chloro-7-indanyloxy)acetic acid (21.7 g., 0.081 mole) in acetic acid (350 ml.). After 15 minutes, the reaction mixture is poured into a solution of sodium bisulfite (20 g.) in water (3000 ml.). The solid product separates, is collected, washed with water, and then dried to yield 23.5 g. of (1-oxo-2-bromo-2-ethyl-4-chloro-7-indanyloxy)acetic acid, m.p. 135.5°–146.5° C. This crude product is used in Step C. A small sample is recrystallized repeatedly from a mixture of acetic acid and water to yield a substantially pure product, m.p. 148°–150° C.

Elemental analysis for $C_{13}H_{12}BrClO_4$: Calc.: C, 44.92; H, 3.48; Found: C, 45.13; H, 3.56.

EXAMPLE 5

(1-Oxo-2-bromo-2-ethyl-6,7-dimethyl-5-indanyloxy)acetic Acid

Step A: (1-Oxo-2-ethyl-6,7-dimethyl-5-indanyloxy)-acetic Acid

By following substantially the procedure described in Example 1, Step A, and using as the reactants [2,3-dimethyl-4-(2-methylenebutyryl)phenoxy]acetic acid (40 g.) and concentrated sulfuric acid (160 ml.), there is obtained 40 g. (100%) of (1-oxo-2-ethyl-6,7-dimethyl-5-indanyloxy)acetic acid which melts at 206° C. after recrystallization from acetonitrile (1.6 l.).

Elemental analysis for $C_{15}H_{18}O_4$: Calc.: C, 68.68; H, 6.92; Found: C, 68.37; H, 6.95.

Step B: (1-Oxo-2-bromo-2-ethyl-6,7-dimethyl-5-indanyloxy)acetic Acid

By following substantially the same procedure as described in Example 1, Step B, using as the reactants (1-oxo-2-ethyl-6,7-dimethyl-5indanyloxy)acetic acid (10.5 g., 0.04 mole), bromine (6.4 g., 0.04 mole), acetic acid (125 ml.) and 48% aqueous hydrobromic acid (2 drops), there is obtained 8.6 g. (63%) of (1oxo-2bromo-2-ethyl-6,7-dimethyl-5-indanyloxy)acetic acid which melts at 136°–139° C. after recrystallization from butyl chloride (200 ml.).

Elemental analysis for $C_{15}H_{17}BrO_4$: Calc.: C, 52.80; H, 5.02; Br, 23.42; Found: C, 52.94; H, 5.26; Br, 23.75.

EXAMPLE 6

[1-Oxo-2-2-bromo-2-ethyl-5-(2,3-dihydro-(1H-benz[e]-indenyloxy)]-acetic Acid Step A: [1-Oxo-2-ethyl-5-(2,3-dihydro-1-H-benz[e]-indenyloxy)]acetic Acid By following substantially the procedure described in Example 1, Step A, and using as the reactants [4-(2-methylenebutyryl)naphthyloxy)acetic acid (25 g.) and concentrated sulfuric acid (100 ml.) there is obtained 15.5 g. (62%) of [1-oxo-2-ethyl-5-(2,3-dihydro-1H-benz-[e]indenyloxy)]acetic acid which after recrystallization from 2-ethoxyethanol (200 ml.) melts at 245°–257° C.

Elemental analysis for $C_{17}H_{16}O_4$: Calc.: C, 71.82; H, 5.67; Found: C, 71.55; H, 5.88.

Step B: [1-Oxo-2-bromo-2-ethyl-5-(2,3-dihydro-1H-benz-[e]indenyloxy)]acetic Acid To a stirred suspension of [1-oxo-2-ethyl-5-(2,3-dihydro-1H-benz[e]indenyloxy)]acetic acid in acetic acid is added a solution of bromine in acetic acid over a period of 30 minutes. The reaction is catalyzed by the addition of 48% hydrobromic acid (2 drops). The reaction mixture is poured into ice containing sodium bisulfite (2.0 g.) whereupon [1-oxo-2-bromo-2-ethyl-5-(2,3-dihydro-1H-benz[e]-indenyloxy)]acetic acid precipitates.

EXAMPLE 7

(1-Oxo-2-bromo-2-cyclohexyl-6,7-dichloro-5-indanyloxy)acetic Acid

Step A: (1-Oxo-2-cyclohexyl-6,7-dichloro-5-indanyloxy)-acetic Acid

By following substantially the procedure described in Example 1, Step A, and by substituting for the (2,3-dichloro-4-(2-methylenebutyryl)phenoxy]acetic acid described therein [2,3-dichloro-4-(2-cyclohexylacryloyl)phenoxy]acetic acid (2.2 g.), there is obtained 2.2 grams of (1-oxo-2-cyclohexyl-6,7-dichloro-5indanyloxy)acetic acid which after recrystallization from nitromethane (15 ml.) melts at 182°–184° C.

Elemental analysis for $C_{17}H_{18}Cl_2O_4$: Calc.: C, 57.16; H, 5.08; Cl, 19.85; Found: C, 57.26; H, 4.82; Cl, 19.58.

Step B: (1-Oxo-2-bromo-2-cyclohexyl-6,7-dichloro-5-indanyloxy)acetic Acid

By following substantially the same procedure as described in Example 1, Step B, the (1-oxo-2-cyclohexyl-6,7-dichloro-5-indanyloxy)acetic acid is brominated to yield (1-oxo-2-bromo-2-cyclohexyl-6,7-dichloro-5-indanyloxy)-acetic acid.

EXAMPLE 8

(1-Oxo-2-ethyl-2,7-dibromo-5-indanyloxy)acetic Acid

Step A: (1-Oxo-2-ethyl-7-bromo-5-indanyloxy)acetic Acid

By following substantially the procedure described in Example 1, Step A, and using as the reactants [3-bromo-4-(2-methylenebutyryl)phenoxy]acetic acid and concentrated sulfuric acid, there is obtained crude product which after recrystallization from acetic acid yields substantially pure (1-oxo-2-ethyl-7-bromo-5-indanyloxy)acetic acid, m.p. 146°–148° C.

Elemental analysis for $C_{13}H_{13}BrO_4$: Calc.: C, 49.86; H, 4.18; Br, 25.52; Found: C, 49.87; H, 4.29; Br, 25.38.

Step B: (1-Oxo-2-ethyl-2,7-dibromo-5-indanyloxy)-acetic Acid

A stirred suspension of (1-oxo-2-ethyl-7-bromo-5-indanyloxy)acetic acid in acetic acid is treated over a 10-minute period with a solution of bromine in acetic acid. The reaction mixture is stirred at ambient temperature for 0.5 hour and poured into water containing sodium bisulfite (1 g.). The (1oxo-2-ethyl-2,7-dibromo-5-indanyloxy)-acetic acid is extracted from the reaction mixture with ether, and the ether solution washed with water and dried over anhydrous magnesium sulfate. Removal of the solvent yields the products as an oil.

EXAMPLE 9

Methyl (1-Oxo-2-ethyl-2,6,7-trichloro-5-indanyloxy)-acetate

Step A: Methyl (1Oxo-2-ethyl-6,7-dichloro-5-indanyloxy)acetate

A solution of (1-oxo-2-ethyl-6,7-dichloro-5-indanyloxy)-acetic acid (138.5 g., 0.457 mole) in methanol (1.5 l.) and containing boron trifluoride etherate (325 g., 2.28 mole) is refluxed for ¾ hour. The solvent is distilled at reduced pressure and the product which remains is filtered, washed with sodium bicarbonate and water and dried. The methyl (1-oxo-2-ethyl-6,7-dichloro-5-indanyloxy)acetate thus obtained (81 g., 73% yield) melts at 134°–137° C. after recrystallization from benzene.

Elemental analysis for $C_{14}H_{14}Cl_2O_4$: Calc.: C, 53.01; H, 4.45; Found: C, 53.16; H, 4.53.

Step B: Methyl (1Oxo-2-ethyl-2,6,7-trichloro-5-indanyloxy)acetate

A stirred solution of cupric chloride dihydrate (4.25 g. and lithium chloride (0.765 g.) in dimethylformamide (10 ml.) is heated to 90° C. and to the mixture is added a solution of methyl (1-oxo-2-ethyl-6,7-dichloro-5-indanyloxy)-acetate (4.7 g., 0.015 mole) in dimethylformamide. The reaction mixture is heated at 90° C. for two hours and poured onto ice. The product is extracted into ether (100 ml.), washed with water, dried over anhydrous sodium sulfate and the ether distilled at reduced pressure. There is thus obtained 2.5 g. of methyl (1-oxo-2-ethyl-2,6,7-trichloro-5-indanyloxy)acetate (53% yield) which melts at 111° C. after recrystallization from methanol.

Elemental analysis for $C_{14}H_{13}Cl_3O_4$: Calc.: C, 47.82; H, 3.73; Found: C, 48.25; H, 3.79.

EXAMPLE 10

(1-Oxo-2-ethyl-2,3,6,7-tetrachloro-5indanyloxy)acetic Acid

Step A: Ethyl (1-Oxo-2ethyl-6,7-dichloro-5indanyloxy)-acetate

A mixture of 2-ethyl-5-hydroxy-6,7-dichloro-1-indanone (9.8 g., 0.04 mole), dimethylformamide (30 ml.), potassium carbonate (12.5 g., 0.09 mole) and ethyl bromoacetate (15 g., 0.09 mole) is stirred and heated on a water bath at 60° C. for one hour. The reaction mixture is poured into ice water (200 ml.) and extracted with two 50 ml. portions of ether. The ether extract is washed with water, dried over magnesium sulfate and the ether distilled at reduced pressure. The ethyl (1-oxo-2-ethyl-6,7-dichloro-5-indanyloxy)acetate thus obtained melts at 116°–118° C. after recrystallization from ethyl alcohol.

Elemental analysis for $C_{15}H_{16}Cl_2O_4$: Calc.: C, 54.40; H, 4.87; Cl, 21.41; Found: C, 54.45; H, 4.60; Cl, 21.51.

Step B: Ethyl (1-Oxo-2-ethyl-6,7-dichloroinden-5-yloxy)acetate

To a solution of ethyl (1-oxo-2-ethyl-6,7-dichloro-5-indanyloxy)acetate (19.8 g., 0.060 mole) in carbon tetrachloride (200 ml.) is added N-bromosuccinimide (11.32 g., 0.0636 mole) and α,α¹-azodiisobutyronitrile (425 mg.). The mixture is heated at reflux for 10 minutes, cooled to room temperature and filtered to remove succinimide. The filtrate is washed with water and then dried over anhydrous magnesium sulfate. The solvent is removed under reduced pressure to afford ethyl (1-oxo-2-ethyl-3-bromo-6,7-dichloro-5-indanyloxy)acetate which is dissolved in pyridine (40 ml.) and heated at 80° C. for 30 minutes. The solution is then cooled to room temperature and poured into 1.2 N hydrochloric acid (400 ml.). The product is extracted with chloroform and the combined extracts are washed with water and dried over anhydrous magnesium sulfate. The solvent is removed under reduced pressure to afford 16.8 g. of a crude product which is then recrystallized from methanol to afford substantially pure ethyl (1-oxo-2-ethyl-6,7-dichloroinden-5-yloxy)acetate, m.p. 141°–143° C.

Step C: (1Oxo-2-ethyl-6,7-dichloroinden-5-yloxy)-acetic Acid

A mixture of ethyl (1-oxo-2-ethyl-6,7-dichloroinden-5-yloxy)acetate, acetic acid (34 ml.) and a 5% hydrochloric acid solution (17 ml.) is heated on a steam bath with stirring for 40 minutes. The reaction solution is cooled to room temperature and diluted with water. The resulting orange solid is then collected and dried to yield 4.08 g. (75%) of crude (1-oxo-2-ethyl-6,7-dichloroinden-5yloxy)-acetic acid. Recrystallization from acetic acid yields a purified (1-oxo-2-ethyl-6,7-dichloroinden-5-yloxy)acetic acid, m.p. 205°–207° C.

Step D: (1-Oxo-2-ethyl-2,3,6,7-tetrachloro-5-indanyloxy)acetic Acid

To a stirred suspension of (1-oxo-2-ethyl-6,7-dichloroinden-5-yloxy)acetic acid (3.03 g., 0.01 mole) in acetic acid (100 ml.) is added a solution of chlorine (1.0 g., 0.014 mole) in acetic acid (50 ml.). The reaction mixture is warmed to 50° C. and then poured into water (600 ml.). The product is extracted into ether, washed with water and dried over anhydrous magnesium sulfate. The ether is then distilled at reduced pressure to afford 1.0 g. of (1-oxo-2-ethyl-2,3,6,7-tetrachloro-5-indanyloxy)acetic acid (27% yield) which melts at 186.5° C. after recrystallization from nitromethane.

Elemental analysis for $C_{13}H_{10}Cl_4O_4$: Calc.: C, 41.97; H, 2.71; Cl, 38.12; Found: C, 42.15; H, 2.78; Cl, 38.20.

EXAMPLE 11

(1-Oxo-2-ethyl-2,3-dibromo-6,7-dichloro-6,7-dichloro-5-indanyloxy)acetic Acid

Bromine (1.45 g., 0.0091 mole) in acetic acid (2.5 g., 0.00825 mole) is added with stirring to a suspension of (1-oxo-2-ethyl-6,7-dichloroinden-5-yloxy)acetic acid (2.5 g., 0.00825 mole) in acetic acid (120 ml.). The reaction mixture is then warmed and treated in the manner described in Example 11, Step D, to afford 3.3 g. (88%) of (1-oxo-2-ethyl-2,3-dibromo-6,7-dichloro-5-indanyloxy)acetic acid which after recrystallization from acetic acid melts at 205.5° C.

Elemental analysis for $C_{13}H_{10}Br_2Cl_2O_4$: Calc.: C, 33.87; H, 2.19; Br, 34.67; Cl, 15.38; Found: C, 34.24; H, 2.52; Br, 34.73; Cl, 15.41.

EXAMPLE 12

(1Oxo-2-isobutyl-2,6,7-trichloro-5-indanyloxy)acetic Acid

Step A: (1Oxo-2-isobutyl-6,7-dichloro-5-indanyloxy)-acetic Acid

[2,3-Dichloro-4-(2-methylene-4-methylvaleryl)-phenoxy]-acetic acid (2.0 g., 0.006 mole) is added with stirring to concentrated sulfuric acid (10 ml.) and the mixture is heated at 60° C. for six hours. The reaction mixture is then cooled and poured into a mixture of ice and water (200 ml.) and the crude product which separates is ground in a mortar, filtered, washed with water and dried. After recrystallization from acetic acid (60 ml.) there is thus obtained 1.7 g. (85% yield) of (1-oxo-2-isobutyl-6,7-dichloro-5-indanyloxy)acetic acid, m.p. 191.5° C.

Elemental analysis for $C_{15}H_{16}Cl_2O_4$: Calc.: C, 54.39; H, 4.87; Found: C, 53.93; H, 4.84.

Step B: (1-Oxo-2-isobutyl-2,6,7-trichloro-5-indanyloxy)-acetic Acid

A solution of glacial acetic acid (50 ml.) and chlorine (0.40 g., 0.00565 mole) is added with stirred over a 10-minute period to a suspension of (1-oxo-2-isobutyl-6,7-dichloro-5-indanyloxy)acetic acid (1.6 g., 0.00485 mole) in glacial acetic acid (50 ml.) and concentrated hydrochloric acid (1 drop). During the addition the reaction vessel is heated on a steam bath. After the addition is complete, the mixture is stirred without heating for 30 minutes and then poured into ice water (200 ml.). The white solid thatseparates is collected by filtration, washed in water and dried to afford 1.0 g. (56% yield) of (1-oxo-2-isobutyl-2,6,7-trichloro-5-indanyloxy)acetic acid which after recrystallization from n-butyl chloride melts at 166° C.

Elemental analysis for $C_{15}H_{15}Cl_3O_4$: Calc.: C, 49.27; H, 4.13; Found: C, 49.18; H, 4.11.

EXAMPLE 13

(1-Oxo-2-2-ethyl-3-methyl-2,6,7-trichloro-5-indanyloxy)acetic Acid

Step A: (1-Oxo-2-ethyl-3-methyl-6,7-dichloro-5-indanyloxy)acetic Acid

[2,3-Dichloro-4-(2-ethylidenebutyryl)phenoxy]acetic acid (22.5 g.) is added with stirring to concentrated sulfuric acid (88 ml.) and heated at 60° C. for six hours. The reaction mixture is then cooled and poured into a mixture of ice and water (1 liter). The crude product which separates is ground in a mortar with water (100 ml.), filtered, washed with water and dried. There is thus obtained 14.5 g. (65% yield) of (1-oxo-2-ethyl-3-methyl-6,7-dichloro-5-indanyloxy)acetic acid, which after recrystallization from nitromethane (75 ml.) melts at 167°-168° C.

Elemental analysis for $C_{14}H_{14}Cl_2O_4$: Calc.: C, 53.01; H, 4.45; Cl, 22.36; Found: C, 53.26; H, 4.36; Cl, 22.10.

Step B: (1-Oxo-2-ethyl-3-methyl-2,6,7-trichloro-5-indanyloxy)acetic Acid

To a suspension of (1-oxo-2-ethyl-3-methyl-6,7-dichloro-5-indanyloxy)acetic acid (3.5 g., 0.011 mole) in glacial acetic acid (75 ml.) and concentrated hydrochloric acid (2 drops) is added, with stirring, a solution of glacial acetic acid (50 ml.) and chlorine (0.9 g., 0.0127 mole) over a period of 10 minutes. During the addition the reaction vessel is heated on a steam bath. After the addition is complete, the mixture is stirred without heating for 30 minutes and then poured into ice water (600 ml.). The white solid that separates is collected by filtration, washed with water and dried. The yield of product is 3.6 g. (93% yield) of (1-oxo-2-ethyl-3-methyl-2,6,7-trichloro-5-indanyloxy)acetic acid which, after recrystallization from nitromethane, melts at 208.5°-210.5° C.

Elemental analysis for $C_{14}H_{13}Cl_3O_4$: Calc.: C, 47.82; H, 3.73; Cl, 30.25; Found: C, 47.70; H, 3.92; Cl, 30.48.

EXAMPLE 14

[1-Oxo-2-chloro-2-ethyl-5-(2,3-dihydro-1H-benz[e]indenyloxy)]acetic Acid

To a suspension of [1-oxo-2-ethyl-5-(2,3-dihydro-1H-benz[e]indenyloxy)]acetic acid (4.2 g., 0.0147 mole) in glacial acetic acid (150 ml.) and concentrated hydrochloric acid (2 drops) is added, with stirring, a solution of glacial acetic acid (50 ml.) and chlorine (0.017 mole) over a period of 10 minutes. During the addition the reaction vessel is heated on a steam bath. When the addition is complete the mixture is stirred without heating for 30 minutes and then poured into ice water (600 ml.) whereupon the crude product separates out. The product is collected by filtration, washed with water and dried to afford 0.6 g. (13% yield) of [1-oxo-2-chloro-2-ethyl-5-(2,3-dihydro-1H-benz-[e]indenyloxy)acetic acid which after recrystallization from a mixture of acetic acid and water melts at 173°-174° C.

Elemental analysis for $C_{17}H_{15}ClO_4$: Calc.: C, 64.07; H, 4.74; Found: C, 64.36; H, 4.80.

EXAMPLE 15

(1-Oxo-2-ethyl-2,6,7-trichloro-5-indanyloxy)acetic Acid

To a suspension of (1-oxo-2-ethyl-6,7-dichloro-5-indanyloxy)acetic acid (6.06 g., 0.02 mole) in glacial acetic acid (100 ml.) and concentrated hydrochloric acid (2 drops) is added, with stirring, a solution of glacial acetic acid (50 ml.) and chlorine (1.56 g., 0.22 mole) over a period of 10 minutes. During the addition the reaction vessel is heated on a steam bath. After the addition is complete, the mixture is stirred without heating for 30 minutes and then poured into ice water (600 ml.). The white solid that separates is collected by filtration, washed with water and dried to afford 6.6 g. (98% yield) of (1-oxo-2-ethyl-2,6,7-trichloro-5-indanyloxy)acetic acid, m.p. 185°–187° C. After recrystallization from acetic acid (25 ml.) the yield of (1-oxo-2-ethyl-2,6,7-trichloro-5-indanyloxy)acetic acid is 5.7 g., m.p. 186°–188° C.

Elemental analysis for $C_{13}H_{11}Cl_3O_4$: Calc.: C, 46.25; H, 3.28; Cl, 31.51; Found: C, 46.40; H, 3.63; Cl, 31.34.

EXAMPLE 16

(1-Oxo-2-isopropyl-2,6,7-trichloro-5-indanyloxy)acetic Acid

Step A: (1-Oxo-2-isopropyl-6,7-dichloro-5-indanyloxy)-acetic Acid 2,3-Dichloro-4-(2-methyleneisovaleryl)phenoxyacetic acid (8.8 g., 0.0278 mole) is added to concentrated sulfuric acid (50 ml.). The mixture is stirred and heated at 60° C. for two hours and then at 80° C. for three hours. The dark solution is cooled and added dropwise with stirring to water (1 l.). A pale yellow gum separates and after 16 hours at 20°–25° C. changes to a cream colored powder (8.6 g., m.p. 161°–164° C.) which is recrystallized from acetic acid-water (1:1) to afford 6.9 g. of (1-oxo-2-isopropyl-7,8-dichloro-5-indanyloxy)acetic acid, m.p. 166°–167.5° C.

Elemental analysis for $C_{14}H_{14}Cl_2O_4$: Calc.: C, 53.02; H, 4.45; Found: C, 53.08; H, 4.60.

Step B: (1Oxo-2-isopropyl-2,6,7-trichloro-5-indanyloxy)-acetic Acid (1-Oxo-2-isopropyl-6,7-dichloro-5-indanyloxy)acetic acid (60 g., 0.189 mole) is dissolved in acetic acid (400 ml.). Sulfuryl chloride (18 ml., 0.216 mole) is added dropwise to the stirred solution. The resulting clear yellow solution is then heated at 80°–85° C. for ¾ hour, cooled and poured slowly, with stirring, into water (3 l.). The gum that separates solidifies after 16 hours to yield 55.5 g. of (1-oxo-2-isoporpyl-2,6,7-trichloro-5-indanyloxy)acetic acid, m.p. 158°–159° C., after recrystallization from acetic acid water (1:1).

Elemental analysis for $C_{14}H_{13}Cl_3O_4$: Calc.: C, 47.82; H, 3.73; Cl, 30.25; Found: C, 47.84; H, 3.71; Cl, 30.31;

EXAMPLE 17

(1-Oxo-2-isopropyl-2,7-dichloro-5indanyloxy)acetic Acid

Step A: (1-Oxo-2-isopropyl-7chloro-5-indanyloxy)-acetic Acid

[3-Chloro-4-(2-methyleneisolvaleryl)phenoxy]acetic acid (12 g., 0.042 mole) is heated in concentrated sulfuric acid (100 ml.) at 65° C. for six hours. The solution is added slowly to water (1 l.) whereupon a gum separates which, after decantation of the aqueous phase, is dissolved in ether. The ether solution is washed well with water, dried (MgSO$_4$) and evaporated to obtain a viscous oil which solidifies very slowly. The solid is recrystallized from benzene-hexane (5:1) and then from benzene to obtain 5.8 g. of (1-oxo-2-isopropyl-7-chloro-5-indanyloxy)acetic acid, m.p. 126°–128° C.

Elemental analysis for $C_{14}H_{15}ClO_4$: Calc.: C, 59.48; H, 5.35; Found: C, 59.66; H, 5.23.

Step B: (1-Oxo-2-isopropyl-2,7-dichloro-5-indanyloxy)-acetic Acid (1-Oxo-2-isopropyl-7-chloro-5-indanyloxy) acid (5.8 g., 0.0205 mole) is chlorinated in acetic acid (50 ml.) with sulfuryl chloride (2 ml., 0.024 mole). The crude product is recrystallized from acetic acid-water (2:3) to obtain 3.3 g. of (1-oxo-2-isopropyl-2,7-dichloro-5-indanyloxy)acetic acid, m.p. 141.5°–142.5° C.

Elemental analysis for $C_{14}H_{14}Cl_2O_4$: Calc.: C, 53.07; H, 4.45; Found: C, 52.90; H, 4.49.

EXAMPLE 18

(1-Oxo-2-cyclopentyl-2,6,7-trichloro-5-indanyloxy)acetic Acid

Step A: (1-Oxo-2-cyclopentyl-6,7-dichloro-5-indanyloxy)-acetic Acid 2,3-Dichloro-4-(2-cyclopentyl-2-methyleneacetyl)-phenoxyacetic acid (20.9 g., 0.061 mole) is added in small portions with stirring to concentrated sulfuric acid (115 ml.). The solution is kept at 60°–65° C. for 4.5 hours, cooled and added dropwise with stirring to water (1.5 l.). The solid that separates is collected, washed well with water and dried under reduced pressure at 65° C. The dried product is recrystallized from acetone-water (16:11) to afford 15.4 g. of (1-oxo-2-cyclopentyl-6,7-dichloro-5-indanyloxy)acetic acid, m.p. 184°–186° C.

Elemental analysis for $C_{16}H_{15}Cl_2O_4$: Calc.: C, 55.99; H, 4.70; Cl, 20.66; Found: C, 55.92; H, 4.81; Cl, 20.69.

Step B: (1-Oxo-2-cyclopentyl-2,6,7-trichloro-5-indanyloxy)acetic Acid (6,7-Dichloro-2-cyclopentyl-1-oxo-5-indanyloxy)acetic acid (15 g., 0.0438 mole) is dissolved in warm acetic acid (150 ml.) and sulfuryl chloride (6.75 g., 0.05 mole) is added slowly with stirring to the warm solution. The mixture is stirred and heated at 80°–85° C. for 1½ hour and then poured into water (1.5 l.). A milky emulsion forms and is dissolved by the addition of 28% ammonium hydroxide (166 ml.). The product separates as a gum and is triturated with water made acidic with 6N hydrochloric acid. The resultant brittle, sticky solid is again suspended in water, the mixture acidified with 6N hydrochloric acid and extracted with ether. The ether extract is dried (Na$_2$SO$_4$) and evaporated. The sticky residue is dissolved in benzene. The benzene solution is cooled and hexane is added in small portions to precipitate the product as a thin oil that eventually solidifies. The solid is digested twice with boiling butyl chloride, taken up in ether, filtered and the ether evaporated. The residual oil is again taken up in benzene and precipitated with hexane. The solid that separates is digested again with hot butyl chloride and dried at 1 mm. at 80° C. over P$_2$O$_5$— and paraffin to afford 10.4 g. of (1-oxo-2-cyclopentyl-2,6,7-trichloro-5-indanyloxy)acetic acid, m.p. 151°–152.5° C.

Elemental analysis for $C_{16}H_{15}Cl_3O_4$: Calc.: C, 50.88; H, 4.00; Found: C, 50.76; H, 3.76.

EXAMPLE 19

(1-Oxo-2-cyclohexyl-2,6,7-trichloro-5-indanyloxy)acetic Acid (1-Oxo-2-cyclohexyl-6,7-diochloro-5-indanyloxy)acetic acid (1.78 g., 0.005 mole) is dissolved in warm acetic acid (30 ml.) and treated dropwise with sulfuryl chloride (0.45 ml., 0.0055 mole). The reaction mixture is heated at 80°–85° C. for one hour, cooled to 20° C. and added with stirring to water (400 ml.). The gummy product is dissolved in ether. The ether solution is washed with water and dried (MgSO$_4$). The ether is evaporated and the residual oil solidifies on triturating with n-butyl chloride. The solid is recrystallized from acetic acid-water (3:2) to afford 0.66 g. of (1-oxo-2-cyclohexyl-2,6,7-trichloro-5-indanyloxy)acetic acid, m.p. 142°–145° C.

Elemental analysis for $C_{17}H_{17}Cl_3O_4$: Calc.: C, 52.13; H, 4.38; Found: C, 52.05; H, 4.38.

EXAMPLE 20

(1-Oxo-2-tert-butyl-2,6,7-trichloro-5-indanyloxy)acetic Acid

Step A: 2′,3′-Dichloro-3,3-dimethyl-4′-hydroxybutyrophenone

To a solution of 2,3-dichloroanisole (44.3 g., 0.25 mole) and 3,3-dimethylbutyryl chloride (37.7 g., 0.28 mole) in dichloromethane (200 ml.) at 5° C. is added with stirring aluminum chloride (37.4 g., 0.28 mole) over a 15-minute period. The mixture is stirred at 0°–5° C. for two hours. Half of the solvent is distilled (100 ml.) and more dichloromethane (2 × 100 ml.) is added and distilled to insure complete removal of hydrogen chloride formed in the reaction. The methoxy group is cleaved by the addition of aluminum chloride (37.4 g., 0.28 mole) and dichloromethane (200 ml.) and refluxing the mixture for five hours. The solvent is decanted and the residue is added with stirring to ice water (500 ml.) containing 12N hydrochloric acid (100 ml.). To insure complete decomposition of the aluminum chloride complex, the mixture is heated to 60° C. with stirring. The reaction mixture is cooled and the aqueous phase is decanted and the residue is dissolved in ether. The ether solution is washed with water, dried ($MgSO_4$) and evaporated. The residue is triturated with petroleum ether, collected and crystallized from ethanol-water (2:1) to obtain 16 g. of 2′,3′-dichloro-3,3-dimethyl-4′-hydroxybutyrophenone, m.p. 156.5° –157.5° C.

Elemental analysis for $C_{12}H_{14}Cl_2O_2$:

Calc.: C, 55.19; H, 5.40; Found: C, 54.99; H, 5.50.

Step B: [2,3-Dichloro-4-(3,3-dimethylbutyryl)phenoxy]-acetic Acid

A mixture of 2′,3′-dichloro-3,3-dimethyl-4′-hydroxybutyrophenone (15.5 g., 0.059 mole) and potassium carbonate (9.7 g., 0.070 mole) in dimethylformamide (DMF) (60 ml.) is stirred at 65° C. for ½ hour. Ethyl bromoacetate (11.7 g., 0.070 mole) is added in one portion and heating and stirring were continued for three hours. A solution of potassium hydroxide (4.6 g., 0.082 mole) in water (80 ml.) is added and the mixture is refluxed for ½ hour. The resulting semisolid mass is added to water (750 ml.). The solution is heated to boiling, filtered, cooled and acidified (HCl) to afford 18 g. of [2,3-dichloro-4-(3,3-dimethylbutyryl)phenoxy]acetic acid, m.p. 145°–145.5° C. after recrystallization from benzene.

Elemental analysis for $C_{14}H_{16}Cl_2O_4$: Calc.: C, 52.68; H, 5.05; Found: C, 52.92; H, 5.12.

Step C: [2,3-Dichloro-4-(2-methylene-3,3-dimethylbutyryl)-acetic acid

A mixture of [2,3-dichloro-4-(3,3-dimethylbutyryl)phenoxy]-acid (17.5 g., 0.055 mole), paraformaldehyde (1.8 g., 0.06 mole), dimethylamine hydrochloride (4.9 g., 0.06 mole) and acetic acid (1 ml.) is heated at 85°–90° C. for sixteen hours. The white solid mass is triturated with acetone (60 ml.) and then with ether. The residue is dissolved in hot water (400 ml.) and filtered. The filtrate is made basic with sodium bicarbonate and heated at 80°–85° C. for three hours. The solid that separates is dissolved by adding an additional 200 ml. of boiling water. The clear, hot solution is acidified (HCl) to afford 4.5 g. of [2,3-dichloro-4-(2-methylene-3,3-dimethylbutyryl)phenoxy]acetic acid, m.p. 160°–162° C. [A sample (0.5 g.) recrystallized from ethanol melted at 162°–164° C.]

Elemental analysis for $C_{15}H_{16}Cl_2O_4$: Calc.: C, 54.40; H, 4.87; Found: C, 53.96; H, 4.96.

Step D: (1-Oxo-2-tert-butyl-6,7-dichloro-5-indanyloxy)-acetic Acid

[2,3-Dichloro-4-(2-methylene-3,3-dimethylbutyryl)phenoxy]acetic acid (4 g., 0.012 mole) is concentrated sulfuric acid (25 ml.) is heated at 65° C. for six hours. The resulting mixture is added dropwise with stirring to water (250 ml.). The resulting solid (3.5 g., m.p. 155°–175° C.) is recrystallized from ethanol-water (1:1) to afford 1.9 g. of (1-oxo-2-tert-butyl-6,7-dichloro-5-indanyloxy)acetic acid, m.p. 186°–188° C.

Elemental analysis for $C_{15}H_{16}Cl_2O_4$: Calc.: C, 54.40; H, 4.87; Found: C, 54.52; H, 4.99.

Step E: (1-Oxo-2-tert-butyl-2,6,7-trichloro-5-indanyloxy)acetic Acid (1-Oxo-2-tert-butyl-6,7-dichloro-5-indanyloxy)acetic acid (1.9 g., 0.0057 mole) is dissolved in warm acetic acid (25 ml.) and sulfuryl chloride (0.55 ml., 0.0066 mole) is added dropwise with stirring. The clear solution is heated at 80°–90° C. for one hour, cooled and added to water. The resulting solid is recrystallized from benzene and from acetic acid-water (1:1) to afford 1.1 g. of (1-oxo-2-tert-butyl-2,6,7-trichloro-5-indanyloxy)acetic acid, m.p. 184°–185.5° C.

Elemental analysis for $C_{15}H_{15}Cl_3O_4$: Calc.: C, 49.27; H, 4.13; Cl, 29.09; Found: C, 49.07; H, 4.27; Cl, 29.22.

EXAMPLE 21

(1-Oxo-2,3-dimethyl-2,6,7-trichloro-5-indanyloxy)acetic Acid

Step A: (1-Oxo-2,3-dimethyl-6,7-dichloro-5-indanyloxy)acetic Acid

[2,3-Dichloro-4-(2-ethylidenepropionyl)phenoxy]acetic acid (18.4 g., 0.061 mole) in concentrated sulfuric acid (110 ml.) is cyclized in the manner of Example 1, Step A, to afford 5.8 g. of (1-oxo-2,3-dimethyl-6,7-dichloro-5-indanyloxy)acetic acid, m.p. 174°–176° C., after recrystallization from ethanol.

Elemental analysis for $C_{13}H_{12}Cl_2O_4$: Calc.: C, 51.50; H, 3.99; Found: C, 51.73; H, 4.03.

Step B: (1-Oxo-2,3-dimethyl-2,6,7-trichloro-5-indanyloxy)acetic Acid (1-Oxo-2,3-dimethyl-6,7-dichloro-5-indanyloxy)acetic acid (6.06 g., 0.02 mole) is dissolved in warm acetic acid (80 ml.) and sulfuryl chloride (2.97 g., 0.022 mole) is added dropwise. The reaction mixture is stirred and heated at 80°–85° C. for one hour and then poured into water (600 ml.). The oil that separates is extracted with ether. The ether extract is washed with water, dried ($MgSO_4$) and evaporated to yield an oil that solidifies on stirring with butyl chloride. The crude product is recrystallized from acetic acid-water (2:1 and 3:1) to afford 3.03 g. of (1-oxo-2,3-dimethyl-2,6,7-trichloro-5-indanyloxy)acetic acid, m.p. 179°–187° C.

Elemental analysis for $C_{13}H_{11}Cl_3O_4$: Calc.: C, 46.25; H, 3.29; Found: C, 46.11; H, 3.26.

EXAMPLE 22

(1-Oxo-2-ethyl-3-phenyl-2,6,7-trichloro-5-indanyloxy)acetic Acid

Step A: 2′,3′-Dichloro-4′-methoxybutyrophenone

A solution of 2′,3′-dichloro-4′-hydroxybutyrophenone (57 g., 0.248 mole) in methanol (400 ml.) is heated to reflux. A solution of sodium hydroxide (40 g. in 100 ml. of water) and dimethyl sulfate are added alternately in small portions over ½ hour to maintain the alkalinity of the reaction mixture. On cooling, a solid separates and is recrystallized from hexane to afford 50.2 g. of 2',3'-dichloro-4'-methoxybutyrophenone, m.p. 42°–44° C.

Elemental analysis for $C_{11}H_{12}Cl_2O_2$: Calc.: C, 53.46; H, 4.89; Found: C, 53.71; H, 4.93.

Step B: 2,3-Dichloro-4-(2-benzylidenebutyryl)anisole

To a mixture of benzaldehyde (19.4 g., 0.183 mole) and 2',3'-dichloro-4'-methoxybutyrophenone (42.2 g., 0.183 mole) in absolute ethanol (350 ml.) a 20% sodium hydroxide solution (35.9 ml.) is added dropwise with stirring. The mixture is stirred for 22 hours. The white solid product that separates is collected and air dried. Yield 55.6 g. (91%), m.p. 127°–130° C.

Elemental analysis for $C_{18}H_{16}Cl_2O_2$: Calc.: C, 64.49; H, 4.81; Found: C, 64.39; H, 4.79.

Step C: 2-Ethyl-3-phenyl-6,7-dichloro-5-methoxyindanone 2,3-Dichloro-4-(2-benzylidenebutyryl)anisole (55.6 g., 0.166 mole) is added with stirring to polyphosphoric acid (550 g.). The mixture is stirred at 95°–100° C. for six hours and at 80°–85° C. for 16 hours. The thick tan mixture is poured into water (2 l.). The solid that separates is collected by filtration, washed with water, dried and recrystallized from absolute ethanol to afford 13.9 g. of 2-ethyl-3-phenyl-6,7-dichloro-5-methoxyindanone, m.p. 111°–116° C. This product is suitable for the next step but when recrystallized from acetic acid-water (6:1) and then from ethanol the product melts at 114°–116° C.

Elemental analysis for $C_{18}H_{16}Cl_2O_2$: Calc.: C, 64.49; H, 4.81; Found: C, 64.48; H, 4.87.

Step D: 2-Ethyl-3-phenyl-5-hydroxy-6,7-dichloroindanone

2-Ethyl-3-phenyl-6,7-dichloro-5-methoxyindanone (13.9 g., 0.0415 mole) is dissolved in heptane (120 ml.) and aluminum chloride (13.8 g., 0.104 mole) is added. The mixture is refluxed and stirred for five hours and then kept at 20°–25° C. for 16 hours. The solvent is decanted, the flask is cooled in an ice bath and 100 ml. of ice water and then 12N HCl (15 ml.) is added to the residue. The gum that separates is extracted with ether, the ether extract is washed with water, dried (MgSO₄) and evaporated to afford 11.3 g. of 2-ethyl-3-phenyl-5-hydroxy-6,7-dichloroindanone. For analysis, a sample is recrystallized from methanol, m.p. 220°–222° C.

Elemental analysis for $C_{17}H_{14}Cl_2O_2$: Calc.: C, 63.57; H, 4.39; Found: C, 63.80; H, 4.46.

Step E: (1-Oxo-2-ethyl-3-phenyl-6,7-dichloro-5-indanyloxy)acetic Acid

To a mixture of 6,7-dichloro-2-ethyl-5-hydroxy-3-phenylindanone (11.3 g., 6.0352 mole) in dimethylformamide (40 ml.) and potassium carbonate (10.2 g., 0.0739 mole) is added dropwise, with stirring, ethyl bromoacetate (12.35 g., 0.0739 mole). The resulting mixture is stirred and heated, at 50°–60° C. for 2½ hours. Then a mixture of potassium hydroxide (5.1 g., 0.091 mole) dissolved in a minimum amount of water and diluted with methanol (40 ml.) is added. The solution is refluxed for three hours and then poured into water (400 ml.). The solution is acidified with 6N hydrochloric acid. The gum that separates solidifies on trituration with water. The crude, air-dried product is recrystallized from benzene and then from ethanol-water (6:5) to afford 1.9 g. of (1-oxo-2-ethyl-3-phenyl-6,7-dichloro-5-indanyloxy)acetic acid, m.p. 199°–203° C.

Elemental analysis for $C_{19}H_{16}Cl_2O_4$: Calc.: C, 60.17; H, 4.25; Found: C, 60.25; H, 4.27.

Step F: (1-Oxo-2-ethyl-3-phenyl-2,6,7-trichloro-5-indanyloxy)acetic Acid (1-Oxo-2-ethyl-3-phenyl-6,7-dichloro-5-indanyloxy)acetic acid (5.6 g., 0.0143 mole) is dissolved in warm acetic acid (70 ml.) and treated with sulfuryl chloride (1.3 ml., 0.016 mole). The solution is heated on a steam bath for two hours, cooled to room temperature and then added slowly to cold water (500 ml.) with stirring. The product precipitates and is collected by suction filtration, washed well with water and air-dried overnight to afford 5.9 g. of crude product. The crude product is recrystallized several times from ethanol (30 ml.) and water (20 ml.) and then from nitromethane to afford substantially pure (1-oxo-2-ethyl-3-phenyl-2,6,7-trichloro-5-indanyloxy)acetic acid, m.p. 190°–192° C.

Elemental analysis for $C_{19}H_{15}Cl_3O_4$: Calc.: C, 55.16; H, 3.66; Found: C, 55.01; H, 3.80.

EXAMPLE 23

(1-Oxo-2-n-propyl-2,6,7-trichloro-5-indanyloxy)acetic Acid

Step A: 2',3'-Dichloro-4'-hydroxyvalerophenone

Aluminum chloride (56 g.) is added over 30 minutes to a stirred mixture of 2,3-dichloroanisole (67 g., 0.38 mole) and valeryl chloride (50 g., 0.042 mole) in dichloromethane (DCM) (250 ml.) at 5° C. After stirring at about 5° C. for an additional two hours the mixture is refluxed for one hour. Then one-half of the DCM is distilled and additional DCM (2 × 100 ml.) is added and distilled. DCM (200 ml.) and aluminum chloride (56.0 g.) are added and the reaction mixture is refluxed for two hours. Then additional aluminum chloride (15.0 g.) is added and refluxing is continued for four hours. The mixture is poured into water (500 ml.), filtered and the DCM layer separated. The aqueous phase is extracted with DCM. The combined extracts are dried (Na₂SO₄) and evaporated. The residue is recrystallized from benzenehexane (3:4) to obtain 31.8 g. of 2',3'-dichloro-4'-hydroxyvalerophenone, m.p. 107°–110° C.

For analysis, a sample is recrystallized further from benzene-cyclohexane (1:6), m.p. 107°–110° C.

Elemental analysis for $C_{11}H_{12}Cl_2O_2$: Calc.: C, 53.46; H, 4.89; Found: C, 53.55; H, 4.92.

Step B: (2,3-Dichloro-4-valerylphenoxy)acetic Acid

Ethyl bromoacetate (20.2 g., 0.1 mole) is added dropwise to a stirred mixture of 2',3'-dichloro-4'-hydroxyvalerophenone (24.7 g., 0.1 mole) and potassium carbonate (16.8 g., 0.12 mole) in dimethylformamide (100 ml.). The mixture is heated at 55°–60° C. for two hours. A solution of potassium hydroxide (8 g., 0.12 mole) in water (50 ml.) and methanol (100 ml.) is added and the reaction mixture is heated at 80°–85° C. for two hours and poured into water. The oil that separates is acidified and extracted with ether. The dried ether solution is evaporated to afford 23.5 g. of (2,3-dichloro-4-valerylphenoxy)acetic acid, m.p. 110°–113° C.

Elemental analysis for $C_{13}H_{14}Cl_2O_4$: Calc.: C, 51.17; H, 4.62; Found: C, 51.02; H, 4.65.

Step C: 2,3-Dichloro-4-(2-methylenevaleryl)phenoxyacetic Acid.

A mixture of 2,3-dichloro-4-valerylphenoxyacetic acid (15.2 g., 0.05 mole), dimethylamine hydrochloride (16.4 g., 0.2 mole), paraformaldehyde (3.5 g., 0.1 mole) and acetic acid (1.3 ml.) is heated at 80°–85° C. for two hours. Dimethylformamide (25 ml.) is added and the heating is continued for two hours. Upon pouring the reaction mixture into water, a white solid separates. This is dissolved in ether. The ether solution is dried ($Na_2SO_4$) and evaporated. The residue is recrystallized from ethyl acetate-cyclohexane (2:6) to afford 12.0 g. of 2,3-dichloro-4-(2-methylenevaleryl)phenoxyacetic acid, m.p. 111°–113° C.

Elemental analysis for $C_{14}H_{14}Cl_2O_4$: Calc.: C, 53.02; H, 4.45; Found: C, 53.21; H, 4.50.

Step D: (1-Oxo-2-n-propyl-6,7-dichloro-5-indanyloxy)-acetic Acid 2,3-Dichloro-4-(2-methylenevaleryl)phenoxyacetic acid (9.5 g., 0.03 mole) is dissolved in concentrated sulfuric acid (50 ml.). The solution is heated for six hours at 60° C. and is added dropwise with stirring to 500 ml. of ice and water. The solid that separates is collected, washed with water and recrystallized from acetic acid-water (2:1) to afford 18.5 g. of (1-oxo-2-n-propyl-6,7-dichloro-5-indanyloxy)acetic acid, m.p. 199°–203° C.

For analysis, a sample is recrystallized further from acetic acid-water to obtain a product of m.p. 203°–205° C.

Elemental analysis for $C_{14}H_{14}Cl_2O_4$: Calc.: C, 53.02; H, 4.45; Found: C, 53.32; H, 4.50.

Step E: (1-Oxo-2-n-propyl-2,6,7-trichloro-5-indanyloxy)acetic Acid (1-Oxo-2-n-propyl-6,7-dichloro-5-indanyloxy)acetic acid (6.7 g., 0.021 mole) is dissolved in acetic acid (75 ml.) and sulfuryl chloride (2 ml.) is added dropwise with stirring. The solution is heated at 80°–85° C. for one hour and poured into water (400 ml.). The solid that separates is washed with water, dried and recrystallized from ethanol-water and then from ethyl acetate-cyclohexane (2:3) to afford 5.3 g. of (1-oxo-2-n-propyl-2,6,7-trichloro-5-indanyloxy)acetic acid, m.p. 185°–187° C.

Elemental analysis for $C_{14}H_{13}Cl_3O_4$: Calc.: C, 47.82; H, 3.73; Found: C, 48.11; H, 3.84.

EXAMPLE 24

(1-Oxo-2-n-pentyl-2,6,7-trichloro-5-indanyloxy)acetic Acid

Step A: 2',3'-Dichloro-4'-hydroxyheptanophenone

By following substantially the procedure described in Example 25, Step A, and by substituting for the valeryl chloride an equimolar quantity of heptanoyl chloride there is obtained a 53% yield of 2',3'-dichloro-4'-hydroxyheptanophenone, m.p. 82°–84° C.

Step B: (2,3-Dichloro-4-heptanoylphenoxy)acetic Acid

By following the procedure of Example 22, Step B, but substituting for the 2',3'-dichloro-2,3-dimethyl-4'-hydroxybutyrophenone there employed an equimolar amount of 2',3'-dichloro-4'-hydroxyheptanophenone there is obtained (2,3-dichloro-4-heptanoylphenoxy)acetic acid, m.p. 104°–105° C. (from benzene) in 67% yield.

Elemental analysis for $C_{15}H_{18}Cl_2O_4$: Calc.: C, 54.07; H, 5.44; Found: C, 54.29; H, 5.42.

Step C: [2,3-Dichloro-4-(2-methyleneheptanoyl)-phenoxy]-acetic Acid

A mixture of the (2,3-dichloro-4-heptanoylphenoxy)acetic acid (42.4 g., 0.127 mole), paraformaldehyde (5.1 g., 0.170 ml.), dimethylamine hydrochloride (10.4 g., 0.127 mole) and acetic acid (2.9 ml.) is heated at 85°–90° C. for 17 hours. Then hot water (1.5 l.) is added. After cooling, the suspended material is removed by ether extraction. The aqueous layer is made basic by the addition of sodium bicarbonate and heated at 80°–90° C. for two hours. Upon acidification (HCl) a gummy solid separates which is triturated with hexane and then recrystallized from cyclohexane and then from carbon tetrachloride to afford 11.2 g. of [2,3-dichloro-4-(2-methyleneheptanoyl)phenoxy]acetic acid, m.p. 103°–106° C.

A sample recrystallized further from benzene-hexane (1:1) has a m.p. 106°–108° C.

Elemental analysis for $C_{16}H_{18}Cl_2O_4$: Calc.: C, 55.66; H, 5.25; Found: C, 55.38; H, 5.33.

Step D: (1-Oxo2--n-pentyl-6,7-dichloro-5-indanyloxy)acetic Acid

[2,3-Dichloro-4-(2-methyleneheptanoyl)phenoxy]acetic acid (11.2 g., 0.0325 mole) is added to concentrated sulfuric acid (60 ml.). The solution is heated at 60°–65° C. for six hours and then added dropwise with stirring to water (1 l.). The tan precipitate is recrystallized from benzene and from acetic acid-water (5:2g) to afford 6.0 g. of (1-oxo-2-n-pentyl-6,7-dichloro-5-indanyloxy)acetic acid, m.p. 192°–195° C. A sample recrystallized further from acetic acid-water melts at 193°–195° C.

Elemental analysis for $C_{16}H_{18}Cl_2O_4$: Calc.: C, 55.66; H, 5.25. Found: C, 55.37; H, 5.30.

Step E: (1-Oxo-2-n-pentyl-2,6,7-trichloro-5-indanyloxy)acetic Acid (1-Oxo-2-n-pentyl-6,7-dichloro-5-indanyloxy)acetic acid (5.7 g., 0.0165 mole) is dissolved in warm acetic acid (80 ml.) and sulfuryl chloride (2.46 g., 0.0182 mole) is added dropwise with stirring. The solution is heated at 80°–90° C. for one hour, cooled and added to water (600 ml.). The solid that separates is recrystallized from acetic acid-water (7:5) and from butyl chloride to afford 3.76 g. of (1-oxo-2-n-pentyl-2,6,7-trichloro-5-indanyloxy)acetic acid, m.p. 122°–124° C.

Elemental analysis for $C_{16}H_{17}Cl_3O_4$: Calc.: C, 50.61; H, 4.51; Found: C, 50.86; H, 4.61.

EXAMPLE 25

(1-Oxo-2-methyl-2,7-dichloro-5-indanyloxy)acetic Acid

Step A: (1-Oxo-2-methyl-7-chloro-5-indanyloxy)acetic Acid

By following substantially the procedure described in Example 1, Step A, using as the reactants [3-chloro-4-(2-methylenepropionyl)phenoxy]acetic acid (40 g., 0.157 mole) and concentrated sulfuric acid (200 ml.) there is obtained 17 g. (42%) of (1-oxo-2-methyl-7-chloro-5-indanyloxy)acetic acid which melts at 170°–172° C. after recrystallization from nitromethane.

Elemental analysis for $C_{12}H_{11}ClO_4$: Calc.: C, 56.59; H, 4.35; Cl, 13.92; Found: C, 56.40; H, 4.33; Cl, 13.78.

Step B: (1-Oxo-2-methyl-2,7-dichloro-5-indanyloxy)acetic Acid

By following substantially the procedure described in Example 12, Step B, using as the reactants (1-oxo-2-methyl-7-chloro-5-indanyloxy)acetic acid (2.55 g., 0.01 mole), chlorine (710 mg., 0.01 mole), glacial acetic acid (50 ml.) and concentrated hydrochloric acid (1 drop) there is obtained (1-oxo-2-methyl-2,7-dichloro-5-indanyloxy)acetic acid.

EXAMPLE 26

(1-Oxo-2-ethyl-2-chloro-3,6,7-trimethyl-5-indanyloxy)acetic Acid

Step A: (1-Oxo-2-ethyl-3,6,7-trimethyl-5-indanyloxy)acetic Acid

By following substantially the procedure described in Example 1, Step A, using as the reactants [2,3-dimethyl-4-(2-ethylidenebutyryl)phenoxy]acetic acid (1.5 g.) and concentrated sulfuric acid (7 ml.) there is obtained 0.7 g. (47%) of (1-oxo-2-ethyl-3,6,7-trimethyl-5-indanyloxy)acetic acid which melts at 141°–143° C. after recrystallization from acetonitrile.

Elemental analysis for $C_{16}H_{20}O_4$: Calc.: C, 69.54; H, 7.29; Found: C, 69.74; H, 7.11.

Step B: (1-Oxo-2-ethyl-2-chloro-3,6,7-trimethyl-5-indanyloxy)acetic Acid

By following substantially the procedure described in Example 12, Step B, using as the reactants (1-oxo-2-ethyl-3,6,7-trimethyl-5-indanyloxy)acetic acid (2.76 g., 0.01 mole), glacial acetic acid (50 ml.), chlorine (710 mg., 0.01 mole) and concentrated hydrochloric acid (1 drop) there is obtained (1-oxo-2-ethyl-2-chloro-3,6,7-trimethyl-5-indanyloxy)acetic acid.

EXAMPLE 27

(1-Oxo-2-methyl-2,6,7-trichloro-5-indanyloxy)acetic Acid

Step A: (1-Oxo-2-methyl-6,7-dichloro-5-indanyloxy)acetic Acid

By following substantially the procedure described in Example 1, Step A, using as the reactants [2,3-dichloro-4-(2-methylenepropionyl)phenoxy]acetic acid (44 g., 0.15 mole) and concentrated sulfuric acid (220 ml.) there is obtained 43 g. (98%) of (1-oxo-2-methyl-6,7-dichloro-5-indanyloxy)acetic acid which melts at 203°–205° C. after recrystallization from acetic acid.

Elemental analysis for $C_{12}H_{10}Cl_2O_4$: Calc.: C, 49.85; H, 3.49; Cl, 24.53; Found: C, 49.99; H, 3.72; Cl, 24.27.

Step B: (1-Oxo-2-methyl-2,6,7-trichloro-5-indanyloxy)acetic Acid

By following substantially the procedure described in Example 12, Step B, and using as the reactants (1-oxo-2-methyl-6,7-dichloro-5-indanyloxy)acetic acid (2.89 g., 0.01 mole), glacial acetic acid (50 ml.), chlorine (710 mg., 0.01 mole) and concentrated hydrochloric acid (1 drop) there is obtained (1-oxo-2-methyl-2,6,7-trichloro-5-indanyloxy)acetic acid.

EXAMPLE 28

2-(1-Oxo-2-ethyl-2,6,7-trichloro-5-indanyloxy)propionic Acid

Step A: 2-[2,3-Dichloro-4-(2-methylenebutyryl)phenoxy]propionic Acid

To a solution of 2,3-dichloro-4-(2-methylenebutyryl)phenol (4.90 g., 0.02 mole) in dimethylformamide (20 ml.) is added potassium carbonate (6.08 g., 0.044 mole) and ethyl 2-bromopropionate (7.97 g., 0.044 mole). The reaction mixture is heated at 55°–60° C. for one hour with stirring. The reaction mixture is cooled. Water (50 ml.) is added and the resulting oil is extracted with ether (3 × 100 ml.). The combined ether extracts are dried over anhydrous magnesium sulfate, filtered and the ether is evaporated under reduced pressure to afford ethyl 2-[2,3-dichloro-4-(2-methylenebutyryl)phenoxy]propionate. The ester is dissolved in ethanol (75 ml.) and treated with a solution of sodium bicarbonate (5.04 g., 0.06 mole) in water (150 ml.). The mixture is heated on a steam bath with stirring for 5 hours and then concentrated under reduced pressure to a volume of 50 ml. Water (50 ml.) is added and the solution is acidified to a pH of 4 with hydrochloric acid (6N). The resulting oil is extracted with ether (3 × 100 ml.) and the combined extracts are dried over anhydrous magnesium sulfate. The ether is evaporated under reduced pressure to afford 6.34 g. (100%) of a white, waxy solid. Recrystallization from cyclohexane affords 5 g. (79%) of crude product, m.p. 115°–119° C. Further purification by recrystallization from butyl chloride affords substantially pure 2-[2,3-dichloro-4-(2-methylenebutyryl)phenoxy]propionic acid, m.p., 122.5°–123.5° C.

Elemental analysis for $C_{14}H_{14}Cl_2O_4$: Calc.: C, 53.02; H, 4.45; Cl, 22.36; Found: C, 52.74; H, 4.46; Cl, 22.19.

Step B: 2-(1-Oxo-2-ethyl-6,7-dichloro-5-indanyloxy)-propionic Acid

By following substantially the procedure described in Example 1, Step A, and using as the reactants 2-[2,3-dichloro-4-(2-methylenebutyryl)phenoxyl]propionic acid (3.17 g., 0.01 mole) and concentrated sulfuric acid (15 ml.) there is obtained 2-(1-oxo-2-ethyl-6,7-dichloro-5-indanyloxy)propionic acid.

Step C: 2-(1-Oxo-2-ethyl-2,6,7-trichloro-5-indanyloxy)-propionic Acid

By following substantially the procedure described in Example 12, Step B, and using as the reactants 2-(1-oxo-2-ethyl-6,7-dichloro-5-indanyloxy)propionic acid (3.17 g., 0.01 mole), glacial acetic acid (50 ml.), chlorine (710 mg., 0.01 mole) and concentrated hydrochloric acid (1 drop) there is obtained 2-(1-oxo-2-ethyl-2,6,7-trichloro-5-indanyloxy)-propionic acid.

EXAMPLE 29

4-(1-Oxo-2-ethyl-2,6,7-trichloro-5-indanyloxy)butyric Acid

Step A: 4-(1-Oxo-2-ethyl-6,7-dichloro-5-indanyloxy)-butyric Acid 6,7-Dichloro-2-ethyl-5-hydroxy-1-indanone (24.5 g., 0.1 mole) and anhydrous potassium carbonate (15.2 g., 0.11 mole) is stirred in dimethylformamide (100 ml.) while ethyl 4-bromobutyrate (21.4 g., 0.1 mole) is added dropwise. The mixture is stirred and heated at 55°–60° C. for two hours. Potassium hydroxide (7.92 g., 0.141 mole) in methanol (60 ml.) is then added. The solid mass that forms is broken up and the mixture is stirred at 80°–85° C. for 1½ hours and poured into water (500 ml.). The aqueous mixture is heated to boiling, filtered and acidified (6N HCl). The solid that separates is collected, washed with water, air-dried and recrystallized from ethylacetate to obtain 25.6 g. of 4-(1(1-oxo-2-ethyl-6,7-dichloro-5-indanyloxy)butyric acid, m.p. 146°–148° C.

Elemental analysis for $C_{15}H_{14}Cl_2O_4$: Calc.: C, 54.40; H, 4.87; Found: C, 54.50; H, 4.87.

Step B: 4-(1-Oxo-2-ethyl-2,6,7-trichloro-5-indanyloxy)-butyric Acid

By following the method of Example 12, Step B, 4-(1-oxo-2ethyl-6,7-dichloro-5-indanyloxy)butyric acid (13.24 g., 0.04 mole) is treated with sulfuryl chloride (3.6 ml., 0.044 mole) in acetic acid (100 ml.) to obtain 9.33 g. of 4-(1-oxo-2-ethyl-2,6,7-trichloro-5-indanyloxy)butyric acid, m.p. 123°–124° C. after recrystallization from ethanol.

Elemental analysis for $C_{15}H_{15}Cl_3O_4$: Calc.: C, 49.27; H, 4.14; Found: C, 49.01; H, 4.11.

EXAMPLE 30

2-(1-Oxo-2-ethyl-2,6,7-trichloro-5-indanyloxy-2-methylpropionic Acid

Step A: 2-(1-oxo-2-ethyl-6,7-dichloro-5-indanyloxy)-2-methylpropionic Acid

2-Ethyl-6,7-dichloro-5-hydroxy-1-indanone (12.3 g., 0.05 mole) is suspended in acetone (500 ml.). The mixture is heated to boiling under nitrogen and solid sodium hydroxide (12.6 g., 0.25 mole) is added with stirring. Chloroform (7.6 g., 0.069 mole) in acetone (50 ml.) is added to the boiling mixture over a 10-minute period. The reaction mixture is refluxed for five hours. The solvent is then removed under reduced pressure. The residue is dissolved in water, the solution is filtered and acidified (HCl) to obtain a tan gum which partially solidifies on triturating in water. The crude product is recrystallized from ethanol-water (1:1) to obtain 5.9 g. of 2-(1-oxo-2-ethyl-6,7-dichloro-5-indanyloxy)-2-methylpropionic acid, m.p. 165°–166° C.

Elemental analysis for $C_{15}H_{16}Cl_2O_4$: Calc.: C, 54.40; H, 4.87; Found: C, 54.54; H, 4.98.

Step B: 2-(1-Oxo-2-ethyl-2,6,7-trichloro-5-indanyloxy)-methylpropionic Acid 2-(1-Oxo-2-ethyl-6,7-dichloro-5-indanyloxy)-2-methylpropionic acid (4.7 g., 0.0014 mole) is dissolved in warm acetic acid (170 ml.) and treated with a solution of chlorine (1.06 g., 0.015 mole) in acetic acid (20 ml.) at 20° C. with stirring. The reaction mixture is kept at 20° C. for one hour and then at 80°0 C. for one hour. The reaction mixture is cooled and added to water (1 l.) with stirring. The white powder that separates is recrystallized from acetic acid-water (4:3) to obtain 3.0 g. of 2-(1-oxo-2-ethyl-2,67-trichloro-5-indanyloxy)-2-methylpropionic acid, m.p. 164.5°–165° C.

Elemental analysis for $C_{15}H_{15}Cl_3O_4$: Calc.: C, 49.27; H, 4.13; Found: C, 49.24; H, 4.14.

EXAMPLE 31

5-(1-Oxo-2-ethyl-2,6,7-trichloro-5-indanyloxymethyl)tetrazole

Step A: (1-Oxo-2-ethyl-6,7-dichloro-5-indanyloxy)-acetonitrile

A mixture of 2-ethyl-5-hydroxy-6,7-dichloroindanone (24.5 g., 0.1 mole), anhydrous potassium carbonate (13.8 g., 0.10 mole), chloroacetonitrile (7.55 g., 0.10 mole) and potassium iodide (1.66 g.) in acetone (0.5 l.) is refluxed for 18 hours. The product which precipitates upon addition of water to the reaction mixture (20 g., 71%) melts at 139°–141° C. after recrystallization from butyl chloride.

Elemental analysis for $C_{13}H_{11}Cl_2NO_2$: Calc.: C, 54.95; H, 3.90; N, 4.93; Found: C, 55.09; H, 3.89; N, 4.92.

Step B: 5-(1-Oxo-2-ethyl-6,7-dichloro-5-indanyloxymethyl)tetrazole

A mixture of (1-oxo-2-ethyl-6,7-dichloro-5-indanyloxy)-acetonitrile (7.5 g., 0.0265 mole), sodium azide (2.02 g., 0.031 mole) and ammonium chloride (1.68 g., 0.0031 mole) in dimethylformamide (40 ml.) is heated on a steam bath for one hour and poured into dilute aqueous hydrochloric acid affording 7.3 g. (85%) of 5-(1-oxo-2-ethyl-6,7-dichloro-5-indanyloxymethyl)tetrazole which melts at 205°–206° C. after recrystallization from nitromethane.

Elemental analysis for $C_{13}H_{12}Cl_2N_4O_2$: Calc.: C, 47.72; H, 3.70; N, 17.13; Found: C, 47.47; H, 3.73; N, 17.30.

Step C: 5-(1-Oxo-2-ethyl-2,6,7-trichloro-5-indanyloxymethyl)tetrazole

A solution of 5-(1-oxo-2-ethyl-6,7-dichloro-5-indanyloxymethyl)tetrazole (2.0 g.) in acetic acid (300 ml.) is warmed to 65° C. on a steam bath and treated during a 10-minute period with a solution of chlorine (700 mg.) in acetic acid (25 ml.). The reaction mixture is heated one hour at 100° C. and the solvent is distilled at reduced pressure to a volume of 50 ml. which on treatment with water affords 0.8 g. (36%) of 5-(1-oxo-2-ethyl-2,6,7-trichloro-5-indanyloxymethyl)tetrazole which melts at 128° C. after recrystallization from ethylacetate and hexane.

Elemental analysis for $C_{13}H_{11}Cl_3N_4O_2$: Calc.: C, 43.18; H, 3.07; N, 15.49; Found: C, 43.00; H, 3.17; N, 15.58.

In a manner similar to that described in Example 1 for the preparation of (1-oxo-2-bromo-2-ethyl-6,7-dichloro-5-indanyloxy) acetic acid and in Example 12 for the preparation of (1-oxo-2-isobutyl-2,6,7-trichloro-5-indanyloxy)acetic acid all of the products of this invention may be obtained. Thus, by substituting the appropriate [4-(2-alkylidenealkanoyl)-phenoxy(or phenylthio)]alkanoic acid for the [2,3-dichloro-4-(2-methylenebutyryl)phenoxy]acetic acid or the [2,3-dichloro-4-(2-methylene-4-methylvaleryl)phenoxy]acetic acid of Example 1, Step A, and Example 12, Step A, respectively, and following substantially the procedure described in Steps A and B of those examples, all of the products of this invention may be obtained. The following equation illustrates the reaction of Example 2, Steps A–C and of Examples 1 and 12, Steps A and B and, together with Table I, infra, depict the [2-(alkylideneacyl)phenoxy(or phenylthio)]alkanoic acid intermediates and the ]1-oxoindanyloxy(and thio)]alkanoic acids (IIIC, infra) and [1-oxo-2-haloindanyloxy (and thio)]alkanoic acid (IId,infra) products derived therefrom:

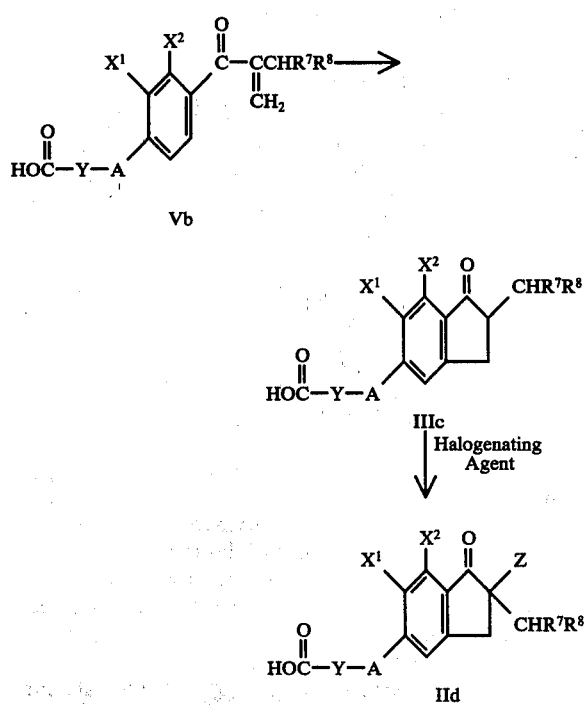

TABLE I

| Ex. No. | A | Y | R⁷ | R⁸ | X¹ | X² | Z |
|---|---|---|---|---|---|---|---|
| 32 | O | —CH₂— | H | CH₃— | H | F | Cl |
| 33 | O | —CH₂— | H | Cl—⟨C₆H₄⟩— | H | Cl | Cl |
| 34 | O | —CH₂— | H | CH₃— | —CH₂CH₂CH₂CH₂— | | Cl |
| 35 | O | —CH₂— | H | CF₃— | CH₃ | —CH₃— | Cl |
| 36 | O | —CH₂— | H | CH₃— | H | —NHC(O)CH₃ | Cl |
| 37 | O | —CH₂— | H | CH₃— | —CH₂CH₂CH₂— | | Cl |
| 38 | O | —CH₂— | H | CH₃— | Cl | —CH₃— | Cl |
| 39 | O | —CH₂— | H | CH₃— | Br | Cl | Cl |
| 40 | O | —CHF— | H | CH₃— | Cl | Cl | Cl |
| 41 | O | —CH₂— | H | CH₃— | H | I | Cl |
| 42 | O | —CH₂— | H | ⟨C₆H₅⟩— | H | Cl | Cl |
| 43 | O | —CH₂— | H | CH₃— | H | CF₃— | Cl |
| 44 | S | —(CH₂)₂— | H | H | H | Cl | Br |
| 45 | S | —CH₂— | H | H | Cl | Cl | Cl |
| 46 | O | —CH₂— | CH₃— | C₂H₅— | Cl | Cl | Cl |

The novel compounds of this invention are diuretic and saluretic agents. Some of these compounds are also able to maintain the uric acid concentration in the blood at pretreatment levels or even cause a decrease in uric acid concentration. The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 50 milligrams of a ]1-oxo-2-halo(or hydrogen)indanyloxy(or thio)]alkanoic acid (I) or a suitable salt, ester or amide derivative thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods and, if desired, can be made up as elixirs or as injectable solutions by methods well known to pharmacists.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form.

The following example is included to illustrate the preparation of a representative dosage form:

| | Per Capsule |
|---|---|
| (1-Oxo-2-isopropyl-6,7-dichloro-5-indanyloxy) acetic Acid | 50 mg. |
| Lactose | 149 mg. |
| Magnesium Stearate | 1 mg. |
| Capsule (Size No. 1) | 200 mg. |

The (1-oxo-2-isopropyl-6,7-dichloro-5-indanyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

It will be apparent from the foregoing description that the [1-oxo-2-halo(or hydrogen)indanyloxy(and thio)]alkanoic acid products (I) of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound having the formula:

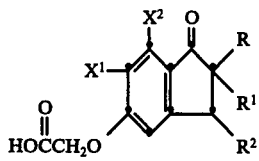

wherein R is lower alkyl containing from 1 to 5 carbon atoms, trifluorosubstituted lower alkyl, cycloalkyl having from 3 to 6 carbon atoms, cycloalkyl lower alkyl having 3 to 6 carbon atoms in the cycloalkyl moiety, R¹ is hydrogen or halo; R² is hydrogen, halo or lower alkyl; X¹ is hydrogen, halo, lower alkyl, or trihalomethyl; X² is halo, lower alkyl or trihalomethyl and the nontoxic, pharmacologically acceptable salt and lower alkyl ester derivatives thereof.

2. A compound having the formula:

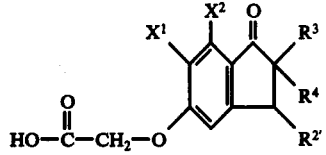

wherein R³ is lower alkyl having from 2 to 4 carbon atoms or cycloaklyl containing from 3 to 6 carbon atoms; R⁴ is hydrogen, chloro or fluoro; R²' is hydrogen; X¹ is methyl or halo; X² is methyl or halo and the nontoxic, pharmacologically acceptable salt and lower alkyl ester derivatives thereof.

3. A compound having the formula:

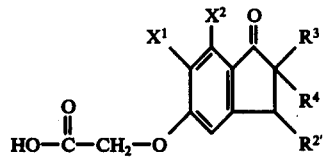

wherein R³ is cycloalkyl having from 3 to 6 carbon atoms or lower alkyl having from 2 to 4 carbon atoms of the formula CHR⁷R⁸ wherein R⁷ is hydrogen or a lower alkyl having from 1 to 2 carbon atoms; R⁸ is lower alkyl having from 1 to 3 carbon atoms; R⁴ is hydrogen, chloro or fluoro; R²' is hydrogen; X¹ is methyl or halo, X² is methyl or halo; and the nontoxic, pharmacologically acceptable salt and lower alkyl ester derivatives thereof.

4. A compound according to claim 2 wherein R³ is lower alkyl containing 2 to 4 carbon atoms or cycloalkyl containing 5 to 6 nuclear carbon atoms; R⁴ is hydrogen or chloro; R²' is hydrogen and X¹ and X² are halo.

5. A compound according to claim 4 wherein R³ is ethyl, R⁴ is chloro, and X¹ and X² are chloro.

6. A compound according to claim 4 wherein R³ is isopropyl; R⁴ is hydrogen, and X¹ and X² are chloro.

7. A compound according to claim 4 wherein R³ is isopropyl; R⁴ is chloro, and X¹ and X² are chloro.

8. A compound according to claim 4 wherein R³ is cyclopentyl; R⁴ is hydrogen, and X¹ and X² are chloro.

9. A compound according to claim 4 wherein R³ is cyclopentyl; R⁴ is chloro, and X¹ and X² are chloro.

10. A compound according to claim 4 wherein R³ is cyclohexyl; R⁴ is hydrogen, and X¹ and X² are chloro.

11. A compound according to claim 4 wherein R³ is cyclohexyl; R⁴ is chloro, and X¹ and X² are chloro.

12. A compound according to claim 4 wherein R³ is n-propyl; R⁴ is hydrogen, and X¹ and X² are chloro.

13. A compound according to claim 4 wherein R³ is n-propyl; R⁴ is chloro, and X¹ and X² are chloro.

* * * * *